(12) United States Patent
Chen et al.

(10) Patent No.: US 8,883,793 B2
(45) Date of Patent: Nov. 11, 2014

(54) TUBULIN INHIBITORS AND METHODS OF USING THE SAME

(75) Inventors: Meng-Hsin Chen, Westfield, NJ (US);
Shih-Hsien Chuang, New Taipei (TW);
Yi-Jen Chen, New Taipei (TW);
Lien-Hsiang Chang, New Taipei (TW);
Tsung-Hui Li, New Taipei (TW);
Ching-Hui Chen, New Taipei (TW);
Win-Yin Wei, New Taipei (TW)

(73) Assignee: Development Center for Biotechnology, New Taipei (TW)

(*) Notice: Subject to any disclaimer, the term of this patent is extended or adjusted under 35 U.S.C. 154(b) by 0 days.

(21) Appl. No.: 13/340,103

(22) Filed: Dec. 29, 2011

(65) Prior Publication Data

US 2012/0172374 A1    Jul. 5, 2012

Related U.S. Application Data

(60) Provisional application No. 61/427,873, filed on Dec. 29, 2010.

(51) Int. Cl.

| | |
|---|---|
| *A61K 31/426* | (2006.01) |
| *A61K 31/4439* | (2006.01) |
| *A61K 31/496* | (2006.01) |
| *C07D 417/12* | (2006.01) |
| *C07D 405/12* | (2006.01) |
| *C07D 277/42* | (2006.01) |
| *C07D 417/04* | (2006.01) |
| *C07D 401/04* | (2006.01) |
| *C07D 409/12* | (2006.01) |
| *C07D 417/06* | (2006.01) |
| *C07D 233/88* | (2006.01) |
| *C07D 417/14* | (2006.01) |
| *C07D 285/135* | (2006.01) |
| *C07D 239/42* | (2006.01) |
| *C07D 213/75* | (2006.01) |
| *C07D 277/46* | (2006.01) |

(52) U.S. Cl.
CPC ............ *C07D 277/46* (2013.01); *C07D 417/12* (2013.01); *C07D 405/12* (2013.01); *C07D 401/04* (2013.01); *C07D 409/12* (2013.01); *C07D 417/06* (2013.01); *C07D 233/88* (2013.01); *C07D 417/14* (2013.01); *C07D 285/135* (2013.01); *C07D 239/42* (2013.01); *C07D 213/75* (2013.01)
USPC ...... 514/254.02; 514/371; 514/342; 514/338; 548/195; 546/270.07; 544/369; 544/331

(58) Field of Classification Search
USPC ............ 514/254.02, 371, 342, 338; 548/195; 546/270.7; 544/369, 331
See application file for complete search history.

(56) References Cited

U.S. PATENT DOCUMENTS 6,784,198 B1    8/2004    Pevarello et al.
2007/0197523 A1*    8/2007    Pacofsky et al. ............ 514/231.2

FOREIGN PATENT DOCUMENTS

WO    WO 2007008541 A2 *    1/2007

OTHER PUBLICATIONS

Krasavin et al., Discovery and Potency Optimization of 2-Amino-5-arylmethyl-1,3-thiazole Derivatives as Potential Therapeutic Agents for Prostate Cancer, 2009, Arch. Pharm. Chem. Life Sci., 342, 420-427.*
PCT International Search Report and Written Opinion dated Aug. 14, 2012, issued by the International Searching Authority in related International Application No. PCT/US2011/067811 (11 pages).
PubChem Compound, datasheet (online Compound Summary), "N-(5-benzyl-1,3-thiazol-2-yl)-3-phenylpropanamide"; CID 1244461; created Jul. 10, 2005; retrieved from the Internet: "URL http://pubchem.ncbi.nlm.nih.gov/search/search.cgi". (3 pages).
PubChem Compound, datasheet (online Compound Summary), "N-(5-benzyl-1,3-thiazol-2-y)-3-(5-methylfuran-2-7l) propanamide"; CID 705778, created Jul. 8, 2005; retrieved from the Internet: "URL: http://pubchem.ncbi.nlm.nih.gov/search/search.cgi". (3 pages).
International Preliminary Report on Patentability dated Jul. 2, 2013, issued in related International Application No. PCT/US2011/067811 (6 pages).

* cited by examiner

*Primary Examiner* — Kristin Vajda
(74) *Attorney, Agent, or Firm* — Osha Liang LLP

(57) ABSTRACT

Compounds represented by the formula (I) or pharmaceutically acceptable salts thereof:

$$R^2\text{—}Y\text{—}Z\text{-}Q\text{-}A\text{-}R^1 \qquad \text{Formula (I)}$$

wherein $R^1$, $R^2$, Y, Z, Q, and A are as defined. These compounds are inhibitors of tubulin polymerization by binding at colchicines binding site and are useful in the treatment of tumors or mitotic diseases such as cancers, gout, and other conditions associated with abnormal cell proliferation.

10 Claims, 7 Drawing Sheets

TUBULIN INHIBITORS AND METHODS OF USING THE SAME

CROSS REFERENCE TO RELATED APPLICATIONS

This application claims priority of U.S. Provisional Patent Application No. 61/427,873, filed on Dec. 29, 2010, the disclosure of which is incorporated by reference in its entirety.

BACKGROUND OF INVENTION

1. Field of the Invention

The invention relates generally to chemical compounds and methods for their use and preparation. In particular, the invention relates to chemical compounds having anti-mitotic activity, and the use of these compounds for treating diseases associated with abnormal cell proliferation, such as tumor.

2. Background Art

Abnormal cell proliferation disorders may include, but are not limited to, tumors, infection, immune rejection response of organ transplant, autoimmune disorders (such as arthritis, lupus, inflammatory bowel disease, Sjogrens syndrome, multiple sclerosis) or a combination thereof. Of these, tumors are perhaps the most well known. Based on the characteristics of cellular behavior, tumors can further be divided into two groups, benign and malignant tumors. Cancer also called malignant tumors can proliferate without respect to normal limits, invading and destroying adjacent tissues, and may even spread to distant anatomic sites through a process called metastasis. These life-threatening, malignant properties of tumors differentiate them from benign tumors, which are self-limited in their growth and do not invade or metastasize.

Anti-mitotic agents interfering with microtubules/tubulin dynamic equilibrium can result in the appearance of typical hallmarks at the level of chromosomes, nuclear membrane, mitotic spindle, and G2/M cells as a consequence of mitotic arrest. Several anti-mitotic agents have had considerable clinical success. For example, vinca alkaloids, such as vincristine and vinblastine, have been used to treat hematological malignancies and non-small-cell lung carcinoma. As another example, taxanes, such as paclitaxcel and docetaxel, have been successfully used to treat breast and non-small-cell lung carcinoma. Despite all these improved results to date, available anti-mitotic agents are inadequate for a number of reasons. For example, use of paclitaxcel or docetaxel can lead to neuropathy. In addition, both the vinca alkaloids and taxanes might induce tumor cells to become drug resistant cells.

There is, therefore, still a need for novel drugs in the treatment of abnormal cell proliferation. Desirable properties of powerful anti-mitotic agent include a good therapeutic index, low cytotoxicity, high bioavailability, easy of synthesis, and no drug resistance.

SUMMARY OF INVENTION

Embodiments of the invention relate to compounds having a structure described by formula (I) or pharmaceutically acceptable salts thereof, as inhibitors of tubulin polymerization by binding at the colchicine binding site and are useful in the treatment of tumor and mitotic diseases, such as in the treatment of cancers, gout, and other conditions associated with abnormal cell proliferation.

$$R^2-Y-Z-Q-A-R^1 \quad \text{Formula (I)}$$

wherein

A is a direct bond or one selected from the group consisting of $(C_{1-6})$alkyl, $(C_{2-6})$alkene, O, S, N—$R^a$, and piperazine;

Q is selected from the group consisting of: $(C_{6-19})$aryl and heteroaryl, wherein said aryl and heteroaryl are each optionally substituted with one or more substituents selected from $R^a$ and $R^b$;

Z is a direct bond or one selected from the group consisting of: $(C_{6-19})$aryl, heteroaryl, $(C_{1-6})$alkyl, $(C_{2-6})$alkene, CONR$^a$, S(O)$_n$NR$^a$, R$^a$NCONR$^a$, R$^a$NS(O)$_n$NR$^a$, R$^a$NC(S)NR$^a$, C(S)NR$^a$, NR$^a$, piperazine, O, and S;

Y is a direct bond or one selected from the group consisting of: $(C_{1-6})$alkyl, $(C_{1-6})$alkoxy, O—$(C_{1-4})$alkyl, S—$(C_{1-4})$alkyl, R$^a$N—$(C_{1-4})$alkyl, and $(C_{2-6})$alkene;

$R^1$ and $R^2$ are independently selected from the group consisting of: halogen, $(C_{6-19})$aryl, heteroaryl, $(C_{2-12})$heterocycloalkyl, $(C_{3-12})$cycloalkyl, $(C_{1-6})$alkyl-$(C_{6-19})$aryl, $(C_{1-6})$alkyl-heteroaryl, $(C_{1-6})$cycloalkyl-$(C_{6-19})$aryl, $(C_{1-6})$cycloakyl-heteroaryl, $(C_{1-6})$alkyl-$(C_{2-12})$heterocycloalkyl, wherein said heteroaryl, $(C_{6-19})$aryl, $(C_{2-12})$heterocycloalkyl and $(C_{3-12})$cycloalkyl are independently, optionally substituted with one or more substituents selected from $R^a$ and $R^b$;

$R^a$ and $R^b$ are each independently selected from the group consisting of hydrogen, halogen, $(C_{1-6})$alkyl, $(C_{1-6})$alkoxyl, O—$(C_{1-6})$alkyl, S—$(C_{1-6})$alkyl, aryl, heteroaryl, N($R^c$)($R^d$), COR$^c$, CON($R^c$)($R^d$), NR$^c$CO—N($R^c$)($R^d$), O—CO—N($R^c$)($R^d$), NR$^c$—S(O)$_n$—N($R^c$)($R^d$), or $R^a$ and $R^b$ can join together with carbon, nitrogen or sulfur atoms, to which they are attached, to form a ring selected from the group consisting of a cycloalkyl and a heterocycloalkyl;

$R^c$ and $R^d$ are each independently selected from the group consisting of hydrogen, halogen, $(C_{1-6})$alkyl, $(C_{1-6})$alkoxyl, $(C_{6-19})$aryl, heteroaryl, $(C_{3-12})$cycloalkyl, or $R^c$ and $R^d$ can join together with carbon, nitrogen or sulfur atoms, to which they are attached, to form a 5-7 membered ring; and n is 0, 1, or 2.

In accordance with some embodiments of the invention, the Z group is —CO—NR$^e$— in the compounds of Formula I and the compounds have a structure described by formula (Ia), or pharmaceutically acceptable salts thereof,

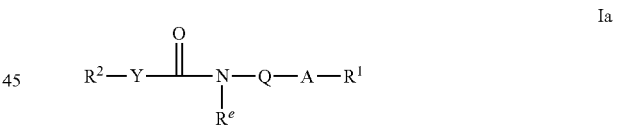

wherein $R^2$, Y, $R^e$, Q, A and $R^1$ are as defined in Formula I.

In accordance with some embodiments of the invention, the Z group is —CO—NH— in the compounds of Formula I and the compounds have a structure described by formula (Ib), or pharmaceutically acceptable salts thereof,

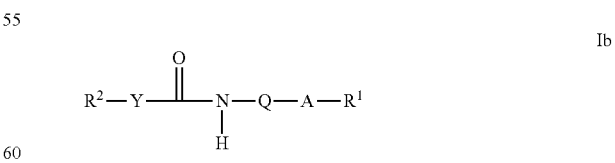

wherein A is selected from the group consisting of $C_{0-4}$ alkyl, $C_{2-4}$ alkenyl, O, S and NH; Q is heteroaryl; Y is absent or selected from $C_{1-4}$ alkyl and $C_{2-4}$ alkenyl; $R^1$ and $R^2$ are each independently selected from the group consisting of aryl, and heteroaryl, wherein said aryl and heteroaryl are each optionally substituted with one or more substituents selected from $R^f$ and $R^g$, wherein $R^f$ and $R^g$ are each independently selected from the group consisting of: hydrogen, halogen, $(C_{1-4})$alkyl, $(C_{1-4})$alkoxyl, O—$(C_{1-4})$alkyl, S—$(C_{1-4})$alkyl, aryl, heteroaryl, $N(R^c)(R^d)$, $COR^c$, $CON(R^c)(R^d)$, $NR^c$CO—$N(R^c)(R^d)$, O—CO—$N(R^c)(R^d)$, $NR^c$—$S(O)_n$—$N(R^c)(R^d)$, or $R^f$ and $R^g$ can join together with carbon, nitrogen or sulfur atoms to which they are attached to form a ring selected from the group consisting of a cycloalkyl and a heterocycloalkyl.

In accordance with some embodiments of the invention, the Z group is —CO—NH— in the compounds of Formula I and the compounds have a structure described by formula (Ic), or pharmaceutically acceptable salts thereof,

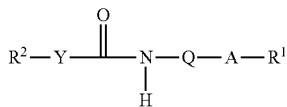

Ic wherein A is selected from the group consisting of $CH_2$, alkenyl, O, S and NH; Q is pyridine, primidine pyrazine, thiazole, pyrrole, imidazole, oxazole, or pyrazole; Y is a direct bond or one selected from $C_{1-2}$ alkyl and alkenyl; $R^1$ and $R^2$ are each independently selected from the group consisting of phenyl, furan, thiophene, pyrrole, thiazole, imidazole, oxadiazole, tiadiazole, pyridine, pyrimidine, pyridazine, pyrazine, indole and naphthalene, wherein each group is optionally substituted with one or more substituents selected from $R^f$ and $R^g$, wherein $R^f$ and $R^g$ are each independently selected from the group consisting of: hydrogen, halogen, $(C_{1-4})$alkyl, $(C_{1-4})$alkoxyl, O—$(C_{1-4})$alkyl, S—$(C_{1-4})$alkyl, aryl, heteroaryl, $N(R^c)(R^d)$, $COR^c$, $CON(R^c)(R^d)$, $NR^c$CO—$N(R^c)(R^d)$, O—CO—$N(R^c)(R^d)$, $NR^c$—$S(O)_n$—$N(R^c)(R^d)$, or $R^f$ and $R^g$ can join together with carbon, nitrogen or sulfur atoms to which they are attached to form a ring selected from the group consisting of a cycloalkyl and a heterocycloalkyl.

In accordance with some embodiments of the invention, the Y group is —$CH_2$—$CH_2$— and the Z group is —CO—NH— in the compounds of Formula I and the compounds have a structure described by formula (Id), or pharmaceutically acceptable salts thereof,

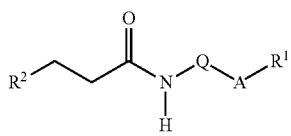

Id wherein A is a direct bond or one selected from the group consisting of $CH_2$, O, and S; Q is pyridine, primidine thiazole, or oxazole; $R^1$ and $R^2$ are each independently selected from the group consisting of phenyl, furan, thiophene, thiazole, pyridine, pyrimidine, indole and naphthalene, wherein each group is optionally substituted with one or more substituents selected from $R^f$ and $R^g$, wherein $R^f$ and $R^g$ are each independently selected from the group consisting of: hydrogen, halogen, $(C_{1-4})$alkyl, $(C_{1-4})$alkoxyl, O—$(C_{1-4})$alkyl, S—$(C_{1-4})$alkyl, aryl, heteroaryl, $N(R^c)(R^d)$, $COR^c$, $CON(R^c)(R^d)$, $NR^c$CO—$N(R^c)(R^d)$, O—CO—$N(R^c)(R^d)$, $NR^c$—$S(O)_n$—$N(R^c)(R^d)$, or $R^f$ and $R^g$ can join together with carbon, nitrogen or sulfur atoms to which they are attached to form a ring selected from the group consisting of a cycloalkyl and a heterocycloalkyl.

In accordance with some embodiments of the invention, the Y group is —$CH_2$—$CH_2$— and the Z group is —CO—NH— in the compounds of Formula I and the compounds have a structure described by formula (Ie), or pharmaceutically acceptable salts thereof,

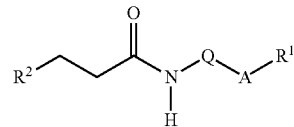

Ie wherein A is a direct bond or one selected from the group consisting of $CH_2$, O, and S; Q is pyridine, primidine or thiazole; $R^1$ and $R^2$ are each independently selected from the group consisting of phenyl, furan, thiophene, and pyridine, wherein each group is optionally substituted with one or more substituents selected from $R^f$ and $R^g$, wherein $R^f$ and $R^g$ are each independently selected from the group consisting of: hydrogen, halogen, $(C_{1-4})$alkyl, $(C_{1-4})$alkoxyl, O—$(C_{1-4})$alkyl, S—$(C_{1-4})$alkyl, aryl, heteroaryl, $N(R^c)(R^d)$, $COR^c$, $CON(R^c)(R^d)$, $NR^c$CO—$N(R^{c)(Rd})$, O—CO—$N(R^c)(R^d)$, $NR^c$—$S(O)_n$—$N(R^c)(R^d)$, or $R^f$ and $R^g$ can join together with carbon, nitrogen or sulfur atoms, to which they are attached, to form a ring selected from the group consisting of a cycloalkyl and a heterocycloalkyl.

In accordance with some embodiments of the invention, in the above compounds, A is not $CH_2$. Instead, A is O or S.

Some embodiments of the invention relate to compositions for inhibiting tubulin polymerization, for treating cancer, for inhibiting vascular capillary formation, or for vascular disrupting, the composition comprises a compound of any of the above-described compounds.

Some embodiments of the invention relate to methods for inhibiting tubulin polymerization, for treating cancer, for inhibiting vascular capillary formation, or for vascular disrupting, using a composition noted above.

DETAILED DESCRIPTION OF THE INVENTION

Figure 1:
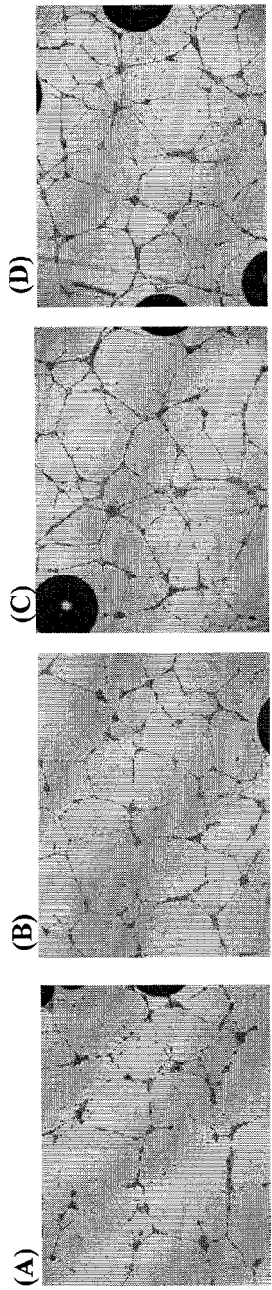
FIGS. 1(A)-1(F) show results of capillary disruption assays in accordance with embodiments of the invention. The images of HUVEC cells treated with compound 70 at 100 nM (A), 30 nM (B), 10 nM (C), and 0 nM (D) for 6.0 hours. (E) Capillary total length of HUVEC cells. Lane 1, 3, 5, 7 were measured before treatments. Lane 2, 4, 6, 8 were measured after treattreatments with compound 70 at 100 nM, 30 nM, 10 nM, and 0 nM for 6.0 hours, respectively. (F) Number of capillary branching points of HUVEC cells. Lane 9, 11, 13, 15 were measured before treatments. Lane 10, 12, 14, 16 were measured after treatments with compound 70 at 100 nM, 30 nM, 10 nM, and 0 nM for 6.0 hours, respectively.
Figure 1:
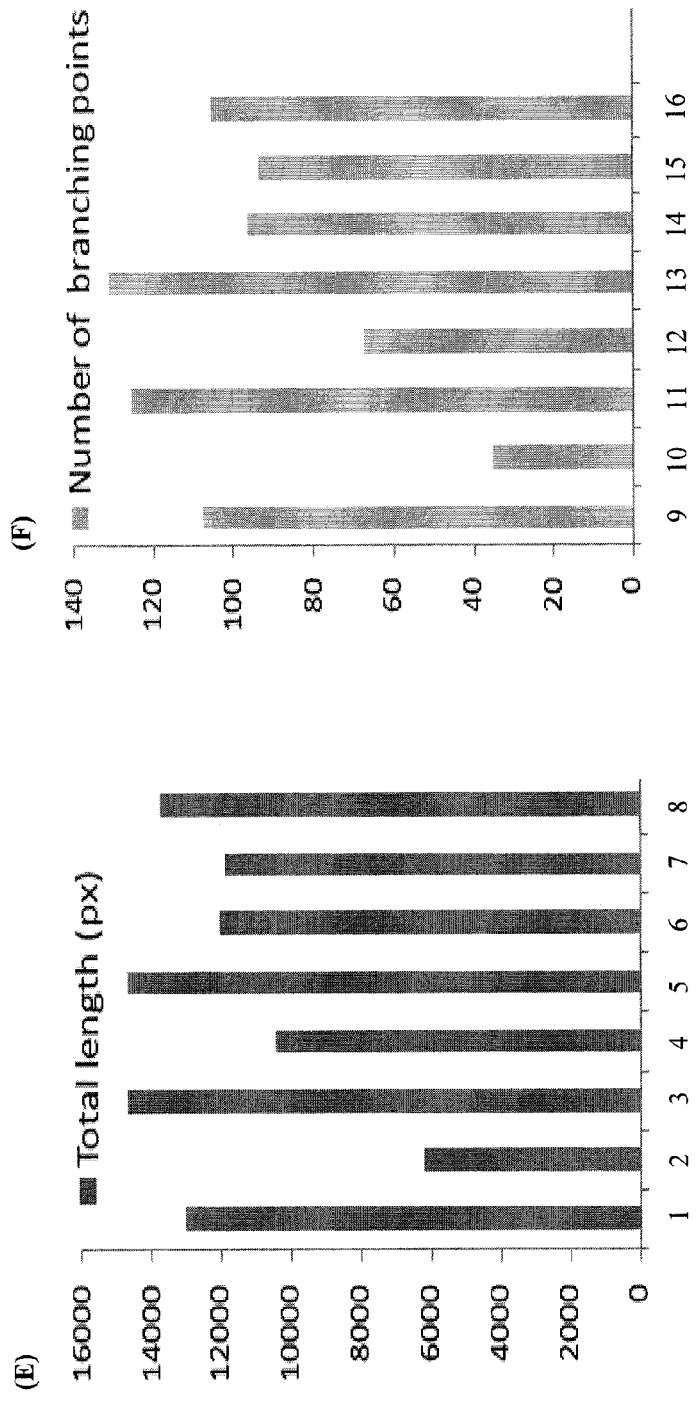

The present invention provides tubulin inhibitor compounds of the formula (I):

$$R^2\text{—}Y\text{—}Z\text{-}Q\text{-}A\text{-}R^1$$

or a pharmaceutically acceptable salt thereof, wherein:
A is absent (i.e., a direct bond) or selected from the group consisting of $(C_{1-6})$alkyl, $(C_{2-6})$alkene, O, S, and N—$R^a$; piperazine.

Q is selected from the group consisting of: $(C_{6-19})$aryl and heteroaryl, wherein said aryl and heteroaryl are each optionally substituted with one or more substituents selected from $R^a$ and $R^b$;

Z is absent (i.e., a direct bond) or selected from the group consisting of: $(C_{6-19})$aryl, heteroaryl, $(C_{1-6})$alkyl, $(C_{2-6})$alkene, CONR$^a$, S(O)$_n$NR$^a$, R$^a$NCONR$^a$, R$^a$NS(O)$_n$NR$^a$, R$^a$NC(S)NR$^a$, C(S)NR$^a$, NR$^a$, piperazine, O, and S;

Y is absent (i.e., a direct bond) or selected from the group consisting of: $(C_{1-6})$alkyl, $(C_{1-6})$alkoxy, O—$(C_{1-4})$alkyl, S—$(C_{1-4})$alkyl, R$^a$N—$(C_{1-4})$alkyl, and $(C_{2-6})$alkene;

$R^1$ and $R^2$ are independently selected from the group consisting of: halogen, $(C_{6-19})$aryl, heteroaryl, $(C_{2-12})$heterocycloalkyl, $(C_{3-12})$cycloalkyl, $(C_{1-6})$alkyl-$(C_{6-19})$aryl, $(C_{1-6})$alkyl-heteroaryl, $(C_{1-6})$cycloalkyl-$(C_{6-19})$aryl, $(C_{1-6})$cycloakyl-heteroaryl, $(C_{1-6})$alkyl-$(C_{2-12})$heterocycloalkyl, wherein said heteroaryl, $(C_{6-19})$aryl, $(C_{2-12})$heterocycloalkyl and $(C_{3-12})$cycloalkyl are independently, optionally substituted with one or more substituents selected from $R^a$ and $R^b$.

$R^a$ and $R^b$ are each independently selected from hydrogen, halogen, $(C_{1-6})$alkyl, $(C_{1-6})$alkoxyl, O—$(C_{1-6})$alkyl, S—$(C_{1-6})$alkyl, aryl, heteroaryl, N(R$^c$)(R$^d$), COR$^c$, CON(R$^c$)(R$^d$), NR$^c$CO—N(R$^c$)(R$^d$), O—CO—N(R$^c$)(R$^d$), NR$^c$—S(O)$_n$—N(R$^c$)(R$^d$), or $R^a$ and $R^b$ can join together with carbon, nitrogen or sulfur atoms to which they are attached to form a ring selected from the group consisting of cycloalkyl and heterocycloalkyl.

$R^c$ and $R^d$ are each independently selected from hydrogen, halogen, $(C_{1-6})$alkyl, $(C_{1-6})$alkoxyl, $(C_{6-19})$aryl, heteroaryl, $(C_{3-12})$cycloalkyl, $R^c$ and $R^d$, or can join together with carbon, nitrogen or sulfur atoms to form a 5-7 membered ring; and n is 0, 1, or 2.

Some embodiments of the present invention relate to compounds having a structure shown as Formula (I), wherein A is absent (i.e., a direct bond) or selected from the group consisting of $(C_{1-4})$alkyl, $(C_{2-4})$alkene, O, S, and N—$R^e$. In accordance with further embodiments of the invention, A is O, S, or N—$R^e$.

Some embodiments of the present invention relate to compounds having a structure shown as Formula (I), wherein Q is heteroaryl, wherein said heteroaryl is optionally substituted with one or more substituents selected from $R^a$ and $R^b$.

Some embodiments of the present invention relate to compounds having a structure shown as Formula (I), wherein Z is absent (i.e., a direct bond) or selected from the group consisting of: $(C_{1-4})$alkyl, CONR$^e$, O, S, and N—$R^e$.

Some embodiments of the present invention relate to compounds having a structure shown as Formula (I), wherein Y is absent (i.e., a direct bond) or selected from the group consisting of: $(C_{1-4})$alkyl and $(C_{2-4})$alkene.

Some embodiments of the present invention relate to compounds having a structure shown as Formula (I), wherein $R^1$ and $R^2$ are each independently selected from the group consisting of: halogen, aryl, heteroaryl, heterocycloalkyl, and cycloalkyl, wherein said aryl, heteroaryl, cycloalkyl $C_{1-2}$alkyl-$(C_{6-19})$aryl, $(C_{1-2})$alkyl-heteroaryl, and heterocycloalkyl are each optionally substituted with one or more substituents selected from $R^a$ and $R^b$.

$R^e$ is selected from the group consisting of: hydrogen, $(C_{1-2})$alkyl, and $(C_{2-4})$alkene.

Some embodiments of the present invention relate to compounds of the Formula Ia:

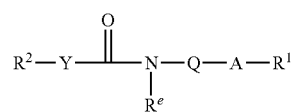

Ia or a pharmaceutically acceptable salt thereof, wherein $R^2$, Y, $R^e$, Q, A and $R^1$ are as defined in Formula I.

Some embodiments of the present invention relate to compounds of the Formula Ib:

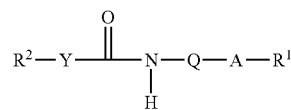

Ib or a pharmaceutically acceptable salt thereof, wherein A is absent (i.e., a direct bond) or selected from the group consisting of $(C_{0-4})$alkyl, $(C_{2-4})$alkenyl, O, S and NH; Q is heteroaryl; Y is a direct bond or one selected from $(C_{1-4})$alkyl and $(C_{2-4})$alkenyl; $R^1$ and $R^2$ are each independently selected from the group consisting of aryl and heteroaryl, wherein aryl and heteroaryl is optionally substituted with one or more substituents selected from $R^f$ and $R^g$;

wherein $R^f$ and $R^g$ are each independently selected from the group consisting of: hydrogen, halogen, $(C_{1-4})$alkyl, $(C_{1-4})$ alkoxyl, O—$(C_{1-4})$alkyl, S—$(C_{1-4})$alkyl, aryl, heteroaryl, $N(R^c)(R^d)$, $COR^c$, $CON(R^c)(R^d)$, $NR^c CO$—$N(R^c)(R^d)$, $O$—$CO$—$N(R^c)(R^d)$, $NR^c$—$S(O)_n$—$N(R^c)(R^d)$, or $R^f$ and $R^g$ can join together with carbon, nitrogen or sulfur atoms to which they are attached to form a ring selected from the group consisting of a cycloalkyl and a heterocycloalkyl;

$R^c$ and $R^d$ are each independently selected from hydrogen, halogen, $(C_{1-4})$alkyl, $(C_{1-4})$alkoxyl, $(C_{6-19})$aryl, heteroaryl, $(C_{3-12})$cycloalkyl, $R^e$ and $R^d$, or can join together with carbon, nitrogen or sulfur atoms to form a 5-7 membered ring; and n is 0, 1, or 2.

Still further embodiments of the present invention relate to compounds of the Formula Ic:

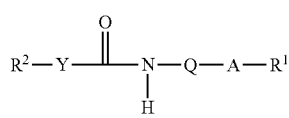

Ic or a pharmaceutically acceptable salt thereof, wherein A is absent (i.e., a direct bond) or selected from the group consisting of $CH_2$, alkenyl, O, S and NH; Q is pyridine, primidine pyrazine, thiazole, pyrrole, imidazole, oxazole and pyrazole; Y is absent (i.e., a direct bond) or selected from $(C_{1-2})$alkyl and alkenyl; $R^1$ and $R^2$ are each independently selected from the group consisting of phenyl, furan, thiophene, pyrrole, thiazole, imidazole, oxadiazole, thiadiazole, pyridine, pyrimidine, pyridazine, pyrazine, indole and naphthalene, wherein each group is optionally substituted with one or more substituents selected from $R^f$ and $R^g$, wherein $R^f$ and $R^g$ are as defined above.

Still further embodiments of the present invention relate to compounds of the Formula Id:

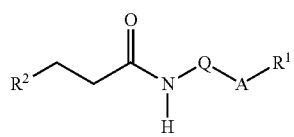

Id or a pharmaceutically acceptable salt thereof, wherein A is absent (i.e., a direct bond) or selected from the group consisting of $CH_2$, O, and S; Q is pyridine, primidine thiazole, and oxazole; $R^1$ and $R^2$ are each independently selected from the group consisting of phenyl, furan, thiophene, thiazole, pyridine, pyrimidine, indole and naphthalene, wherein each group is optionally substituted with one or more substituents selected from $R^f$ and $R^g$, wherein $R^f$ and $R^g$ are as defined above.

Some embodiments of the present invention relate to compounds of the Formula Ie:

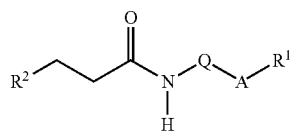

Ie or a pharmaceutically acceptable salt thereof, wherein A is absent (i.e., a direct bond) or selected from the group consisting of $CH_2$, O, and S. Q is pyridine, primidine and thiazole; $R^1$ and $R^2$ are each independently selected from the group consisting of phenyl, furan, thiophene, and pyridine, wherein each group is optionally substituted with one or more substituents selected from $R^f$ and $R^g$, wherein $R^f$ and $R^g$ are as defined above.

Some embodiments of the invention relate to the above compounds, in which A is not $CH_2$. Instead, A may be O or S.

The term "acetal" means a functional group or molecule containing a CH bounded to two —OR groups. A "cyclic acetal" thus means a cyclic or ring structure containing an acetal group.

The term "ketal" means a functional group or molecule containing a carbon bonded to two —OR groups. A "cyclic ketal" thus means a cyclic or ring structure containing a ketal group.

The term "alkyl" means carbon chains that have no double or triple bonds, and that may be linear, branched or a combination thereof. An "alkyl" group may be further defined by the number of carbons in the group, such as $C_1$-$C_3$ alkyl, $C_1$-$C_6$ alkyl, $C_1$-$C_{12}$ alkyl, and so on. For example, $C_1$-$C_6$ alkyl is defined as an alkyl group having 1, 2, 3, 4, 5 or 6 carbons in an arrangement that is linear, branched, or a combination thereof. In this description, the number of carbons may be denoted as "$C_1$-$C_6$" or "$C_{1-6}$"—i.e., these two notations may be used interchangeably. Examples of alkyl groups include methyl, ethyl, propyl, n-propyl, isopropyl, butyl, sec- and tert-butyl, pentyl, hexyl, heptyl, and the like. Similarly, the term "$C_0$-$C_4$ alkyl" includes alkyls containing 4, 3, 2, 1, or no carbon atoms. An alkyl group with no carbon atoms is a hydrogen atom substituent when the alkyl is a terminus moiety. An alkyl with no carbon atoms is a direct bond when the alkyl is a bridging moiety.

In this description, "alkyl" is used in a broad sense to include "alkylenyl,"—i.e., a bivalent alkyl group linking two other residues. Examples of such bivalent "alkyl" include: —$CH_2$—, —$CH_2$—$CH_2$—, etc.

The term "alkene" or "alkenyl" means a linear or branched structure or a combination thereof, having at least one carbon-to-carbon double bond. An "alkene" group may be further defined by the number of carbons in the group, such as $C_2$-$C_6$ alkene, $C_2$-$C_{12}$ alkene, and so on. A $C_2$-$C_6$ alkene, for example, includes ethylene, propylene, 1-methylethylene, butylenes, and the like. A $C_2$-$C_6$ alkenyl, for example, includes ethylenyl, propylenyl, 1-methylethylenyl, butylenyl, and the like. Similarly, "alkenyl" may be used in a broad sense to include bivalent "alkenyl" that links two residues.

The term "alkynyl" means a linear or branched structure, or a combination thereof, having at least one carbon-to-carbon triple bond. An "alkynyl" group may be further defined by the number of carbons in the group, such as $C_2$-$C_6$ alkynyl, $C_2$-$C_{12}$ alkynyl, and so on. For example, $C_2$-$C_6$ alkynyl is defined as a group having 2, 3, 4, 5 or 6 carbon in a linear or branched arrangement. Thus, $C_2$-$C_6$ alkynyl includes 2-hexynyl, 2-pentynyl, or the like.

The term "alkoxy" as used herein, alone or in combination, includes an alkyl group, as defined above, connected to an oxy connecting atom. The term "alkoxy" also includes alkyl ether groups, where the term "alkyl" is as defined above, and "ether" means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as "dimethyl ether"), and methoxyethane (also referred to as "ethyl methyl ether").

The term "amine," unless specifically stated otherwise, includes primary, secondary and tertiary amines. An amine may include one or more alkyl, alkenyl, alkynyl, or aryl groups, as defined herein.

The term "aryl," unless specifically stated otherwise, is intended to mean any stable monocyclic or fused carbon rings of up to 7 members in each ring, wherein at least one ring is aromatic. An "aryl" group may be further defined by the number of carbons in the group, such as $(C_{6-12})$aryl, $(C_{6-19})$aryl, and so on. Example of such aryl groups include phenyl, naphthyl and tolyl.

The term "aryloxy" means an aryl group as defined above connected through an oxygen atom. Unless specifically stated otherwise, an aryloxy group includes a multiple ring system as well as a single ring system, such as, for example, phenyl or naphthyl, connected through the oxy connecting atom to a connecting site.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. An "cycloalkyl" group may be further defined by the number of carbons in the group, such as $(C_{3-6})$cycloalkyl, $(C_{3-12})$cycloalkyl, $(C_{3-19})$cycloalkyl, and so on. Examples of cycloalkyl include cyclopropyl, cyclobutyl, cyclopentyl, cyclohexyl, decahydronaphthalenyl, adamantanyl, indanyl, indenyl, fluorenyl, 1,2,3,4-tetrahydronaphthalenyl, and the like.

Similarly, "cycloalkenyl" means carbocycles containing no heteroatoms and at least one nonaromatic C—C double bone. Cycloalkenyl may include mono-, bi- and tricyclic partially saturated carbocycles, as well as benzofused cycloalkenes. An "cycloalkenyl" group may be further defined by the number of carbons in the group, such as $(C_{3-6})$cycloalkenyl, $(C_{3-12})$cycloalkenyl, $(C_{3-19})$cycloalkenyl, and so on. Examples of cycloalkenyl include cyclohexenyl, indenyl, and the like.

The term "cycloalkyloxy," unless specifically stated otherwise, includes a cycloalkyl group as defined above connected to an oxy connecting atom.

The term "hetero," unless specifically stated otherwise, includes one or more O, S, N atoms, and a combination of such atoms. For example, "heterocycloalkyl" (or heterocyclyl) and "heteroaryl" include ring systems that contain one or more O, S, and/or N atoms in the ring. The hetero atoms in these ring systems replace ring carbon atoms.

The term "heterocycloalkyl" means a clycolalkyl as defined above, in which one or more ring carbons are replaced with hetero atoms, such as O, S, and/or N. Examples of heterocycloalkyl include azetidinyl, pyrrolidinyl, piperidinyl, piperazinyl, morpholinyl, tetrahydrofuranyl, imidazolinyl, cyclic acetals, cyclic ketals, pyrrolidin-2-one, piperidin-2-one and thiomorpholinyl. As used herein, "heterocycloalkyl" includes bridged heterocycloalkyls having two or more heterocycloalkyl groups joined via adjacent or non-adjacent atoms.

The term "heteroaryl" as used herein, except as otherwise noted, is intended to mean a monocyclic or multicyclic ring system containing at least one aromatic ring and from one to four heteroatoms selected from the group consisting of N, O and S, wherein the nitrogen and sulfur heteroatoms may optionally be oxidized, and the nitrogen heteroatom may optionally be quaternized. Examples of a heteroaryl may include a stable 5-7 membered monocyclic- or a stable 9-10 membered fused bicyclic heterocyclic ring system, which contains an aromatic ring. The heteroaryl group may be defined by the number of carbons included therein. For example, $(C_{3-19})$heteroaryl refers to a heteroaryl group having form 3 to 19 carbons, in addition to the hetero atom(s). Some ring(s) of a multicyclic ring system may be saturated, partially saturated, or unsaturated. A heteroaryl group includes any bicyclic or multicyclic group in which ad heterocyclic ring is fused to an aromatic ring (such as a benzene ring). The heterocyclic ring may be attached at any heteroatom or carbon atom which results in the creation of a stable structure. Examples of such heteroaryl groups include, but are not limited to, pyridine, pyrimidine, pyrazine, thiophene, oxazole, thiazole, triazole, thiadiazole, oxadiazole, pyrrole, 1,2,4-oxadiazole, 1,3,4-oxadiazole, 1,2,4-thiadiazole, 1,3,4-thiadiazole, and 1,2,4-triazole.

Additional examples of heteroaryl include quinolinyl, pyrimidinyl, isoquinolinyl, pyridazinyl, quinoxalinyl, furyl, benzofuryl, dibenzofuryl, thienyl, benzothienyl, indolyl, indazolyl, isoxazolyl, isothiazolyl, imidazolyl, benzimidazolyl, thiadiazolyl, tetrazolyl.

The term "heteroaryloxy," unless specifically stated otherwise, describes a heteroaryl group, as defined above, connected through an oxy connecting atom to a connecting site.

The above described ring systems, such as cycloalkyl, heterocycloalkyl, aryl, and heteroaryl, may be further connected to a non-cyclic moiety, such as an alkyl, alkenyl, or alkynyl. In these cases, the cyclic and non-cyclic parts may be separately denoted by the numbers of carbons in each part. For example, $(C_{3-19})$heteroaryl$(C_{1-6})$alkyl defines a heteroaryl ring having 3-19 carbon atoms attached to an alkyl group having 1-6 carbons.

Examples of $(C_{3-19})$heteroaryl$(C_{1-6})$alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Unless otherwise stated, the term "carbamoyl" is used to include —NHC(O)O($C_{1-4}$)alkyl, and —OC(O)NH($C_{1-4}$)alkyl.

The term "halogen" or "halide" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, the substitution can be made at any or all subparts in a molecule. For example, a substituted aryl($C_{1-6}$)alkyl may include one or more substitutions on the aryl group and/or one or more substitutions on the alkyl group.

The term "oxide" of heteroaryl or heterocycloalkyl groups is used in the ordinary well-known chemical sense and include, for example, N-oxides of nitrogen atoms or S-oxides of sulfur atoms.

When a group is "absent," the group is "a direct bond" linking the two neighboring groups.

Compounds described herein having one or more double bonds may give rise to cis/trans isomers as well as other conformational isomers. The present invention includes all such possible isomers, as well as mixtures of such isomers.

Unless specifically stated otherwise or indicated by a bond symbol (dash or double dash), the connecting point to a recited group will be on the right-most stated group. That is, for example, a phenylalkyl group is connected to the main structure through the alkyl.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specifics stereoisomers are also included. During the course of the synthetic procedures used to prepare such compounds, or in using racemization or epimerization procedures known to those skilled in the art, the products of such procedures can be mixtures of stereoisomers.

The compounds of the present invention are useful in various pharmaceutically acceptable salt forms. The term "pharmaceutically acceptable salts" refer to those salt forms which would be apparent to pharmaceutical chemists, i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

The pharmaceutically acceptable salts may be prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese, potassium, sodium, zinc, and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethanmine, and the like.

When a compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized by conventional chemical methods. Generally, the salts are prepared by reacting the free bases or acids with stoichiometric amounts or with an excess of the desired salt-forming inorganic or organic acids or bases, in a suitable solvent or solvent combination.

The invention described herein also includes pharmaceutical compositions which comprise compounds described by Formula (I), or pharmaceutically acceptable salts thereof, in combination with pharmaceutically acceptable carriers.

Exemplary strategies for the preparation of invention compounds are depicted in Scheme I. The numbering conventions for the "$R^1$", "$R^2$", "$R^4$", "Y", "A" and "Q" are as provided for in the compounds of Formula (I), and "X" represents halogen.

As depicted in synthetic routes in Scheme 1, the carboxylic acid derivatives I-1 are commercially available or can be prepared by the literature methods. Many of the amino heteroaryl bromide compounds I-2 are commercially available, such as 2-amino-5-bromo-thiazole, 2-amino-5-bromo-pyridine, 2-amino-5-bromo-pyrimidine, 2-amino-5-bromo-3-methyl-pyridine. Other amino heteroaryl halides can be prepared by conventional methods familiar to those skilled in the art. Coupling of compound I-1 and I-2 may be conveniently carried out in an inert solvent, such as dichloromethane, by a coupling reagent, such as DCC or EDC, in the presence of HOBt. Alternatively, the coupling can also be effected with acid chloride which may be prepared using compound I-1 and oxalyl chloride, and compound I-2 in an appropriated solvent, such as pyridine. Separation of unwanted side products and purification of intermediates may be achieved by chromatography on silica gel, employing flash chromatography (W. C. Still, M. Kahn and A. Mitra J. Org. Chem. 1978, 43, 2923) and MPLC. Compound I-3 can then be converted into compound I-4 via appropriate chemical reactions familiar to those skilled in the art, such as, but not limit to, Suzuki reaction, Nigishi reaction, Stille reaction, Heck reaction, Buchwald-Hartwig reaction, and Ullmann reaction, to produce the final inhibitors.

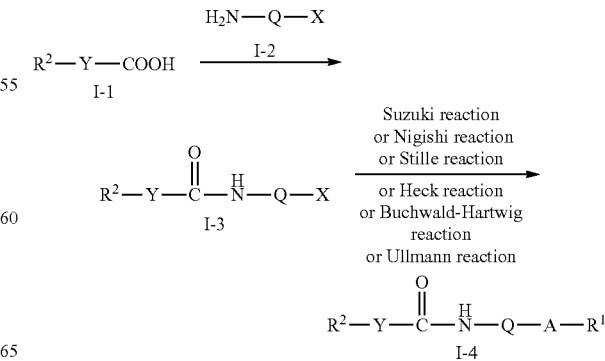

Many amino heteroaryl halides such as compound II-5 are commercially available or can be synthesized by conventional methods familiar to those skilled in the art (for example English et al. J. Am. Chem. Soc., 1946, 68, pp. 453 and 457). Reaction between compound II-5 and A-R¹ can be achieved by using known methods, such as substitution reaction under basic condition or Pd-mediated coupling reactions to give compound II-6. The amino group of compound II-6 can further react with isocyanates to yield urea derivatives 11-7 or react with chloroformates in the presence of triethylamine or pyridine of give carbamate derivatives II-7. When amide derivatives II-7 are desired, the amino intermediate II-6 can be converted to target final compound II-7 by standard peptide coupling conditions (Scheme 2).

Scheme 2

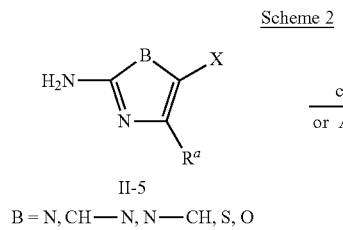

II-5
B = N, CH—N, N—CH, S, O

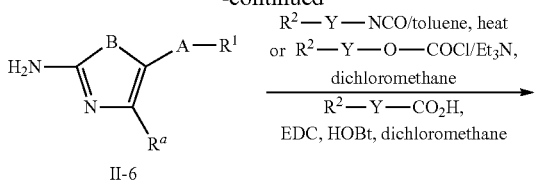

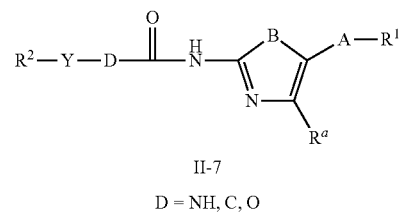

II-7
D = NH, C, O

Other aspects and advantages of the invention will be apparent from the following examples, description and the appended claims.

Representative examples of compounds of formula I are set forth below in Table 1:

TABLE 1

| Compd ID | Structure |
|---|---|
| 1 | N-(5-Benzyl-thiazol-2-yl)-3-(5-methyl-furan-2-yl)-propionamide |
| 2 | N-(5-Benzyl-thiazol-2-yl)-3-phenyl-propionamide |
| 3 | N-(5-Benzyl-thiazol-2-yl)-3-phenyl-acrylamide |

TABLE 1-continued
| Compd ID | Structure |
|---|---|
| 4 | 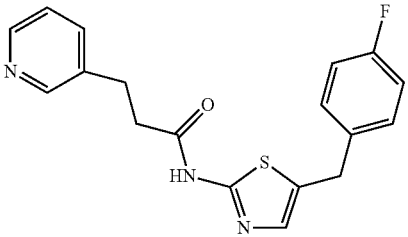 [SMILES: O=C(CCc1cccnc1)Nc1ncc(Cc2ccc(F)cc2)s1]<br>N-[5-(4-Fluoro-benzyl)-thiazol-2-yl]-3-pyridin-3-yl-propionamide |
| 5 | 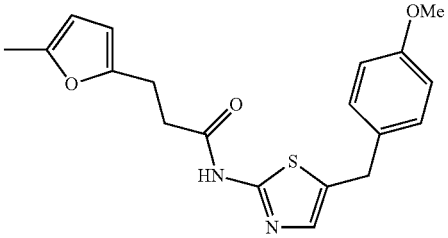 [SMILES: COc1ccc(Cc2cnc(NC(=O)CCc3ccc(C)o3)s2)cc1]<br>N-[5-(4-Methoxy-benzyl)-thiazol-2-yl]-3-(5-methyl-furan-2-yl)-propionamide |
| 6 | 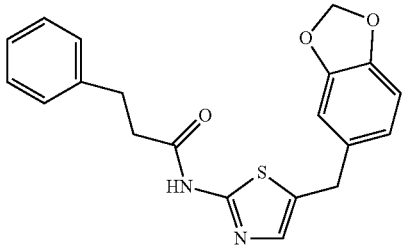 [SMILES: O=C(CCc1ccccc1)Nc1ncc(Cc2ccc3c(c2)OCO3)s1]<br>N-(5-Benzo[1,3]dioxol-5-ylmethyl-thiazol-2-yl)-3-phenyl-propionamide |
| 7 | 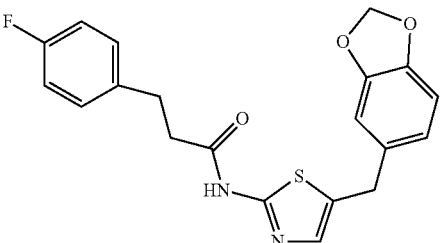<br>N-(5-Benzo[1,3]dioxol-5-ylmethyl-thiazol-2-yl)-3-(4-fluoro-phenyl)-propionamide |
| 8 | 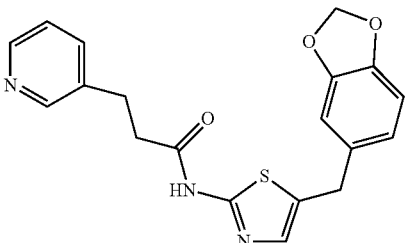<br>N-(5-Benzo[1,3]dioxol-5-ylmethyl-thiazol-2-yl)-3-pyridin-3-yl-propionamide |

TABLE 1-continued
| Compd ID | Structure |
|---|---|
| 9 | 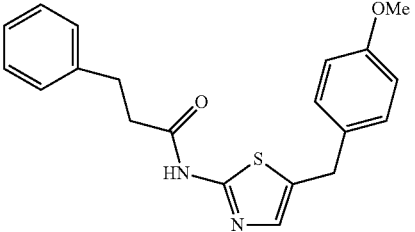 [SMILES: COc1ccc(Cc2cnc(NC(=O)CCc3ccccc3)s2)cc1]<br>N-[5-(4-Methoxy-benzyl)-thiazol-2-yl]-3-phenyl-propionamide |
| 10 | 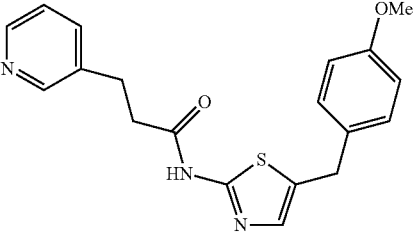 [SMILES: COc1ccc(Cc2cnc(NC(=O)CCc3cccnc3)s2)cc1]<br>N-[5-(4-Methoxy-benzyl)-thiazol-2-yl]-3-pyridin-3-yl-propionamide |
| 11 | 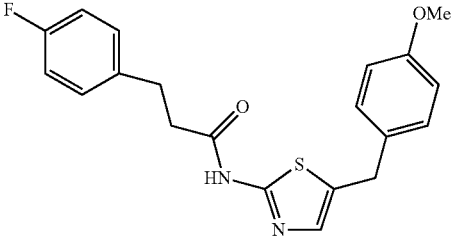 [SMILES: COc1ccc(Cc2cnc(NC(=O)CCc3ccc(F)cc3)s2)cc1]<br>3-(4-Fluoro-phenyl)-N-[5-(4-methoxy-benzyl)-thiazol-2-yl]-propionamide |
| 12 | 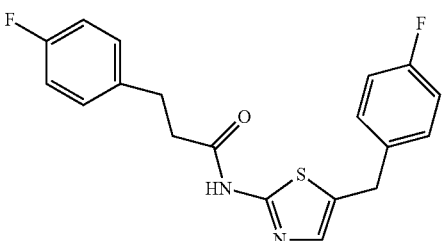<br>N-[5-(4-Fluoro-benzyl)-thiazol-2-yl]-3-(4-fluoro-phenyl)-propionamide |
| 13 | 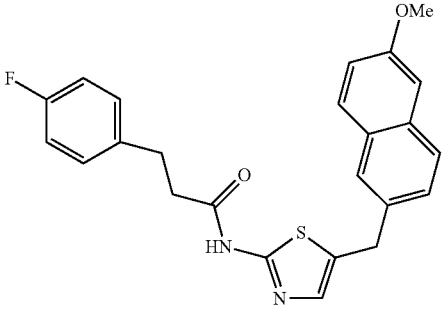 [SMILES: COc1ccc2cc(Cc3cnc(NC(=O)CCc4ccc(F)cc4)s3)ccc2c1]<br>3-(4-Fluoro-phenyl)-N-[5-(6-methoxy-naphthalen-2-ylmethyl)-thiazol-2-yl]-propionamide |

TABLE 1-continued
| Compd ID | Structure |
|---|---|
| 14 | 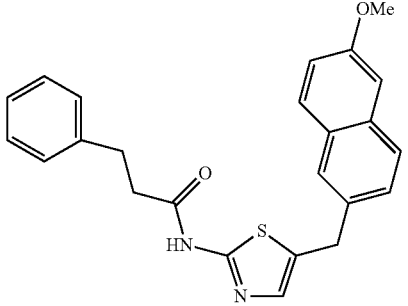 [SMILES: COc1ccc2cc(Cc3cnc(NC(=O)CCc4ccccc4)s3)ccc2c1]<br>N-[5-(6-Methoxy-naphthalen-2-ylmethyl)-thiazol-2-yl]-3-phenyl-propionamide |
| 15 | 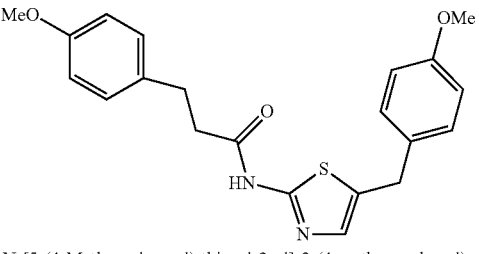<br>N-[5-(4-Methoxy-benzyl)-thiazol-2-yl]-3-(4-methoxy-phenyl)-propionamide |
| 16 | 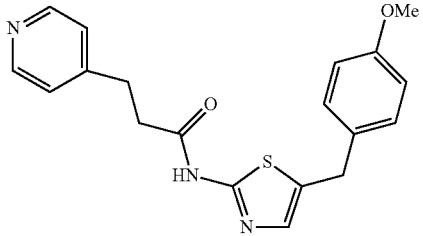 [SMILES: COc1ccc(Cc2cnc(NC(=O)CCc3ccncc3)s2)cc1]<br>N-[5-(4-Methoxy-benzyl)-thiazol-2-yl]-3-pyridin-4-yl-propionamide |
| 17 | 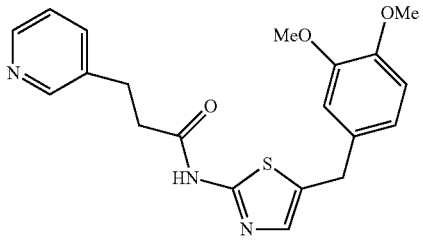 [SMILES: COc1ccc(Cc2cnc(NC(=O)CCc3cccnc3)s2)cc1OC]<br>N-[5-(3,4-Dimethoxy-benzyl)-thiazol-2-yl]-3-pyridin-3-yl-propionamide |
| 18 | 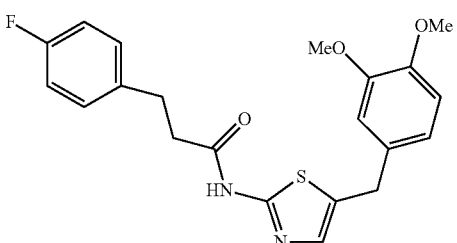<br>N-[5-(3,4-Dimethoxy-benzyl)-thiazol-2-yl]-3-(4-fluoro-phenyl)-propionamide |

TABLE 1-continued
| Compd ID | Structure |
|---|---|
| 19 | 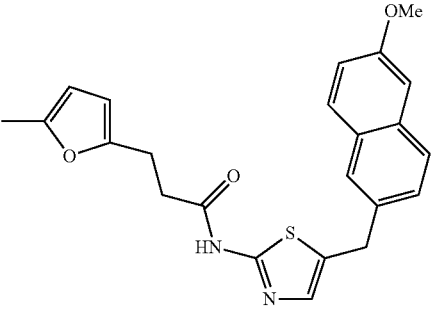 [SMILES: COc1ccc2cc(Cc3cnc(NC(=O)CCc4ccc(C)o4)s3)ccc2c1]
N-[5-(6-Methoxy-naphthalen-2-ylmethyl)-thiazol-2-yl]-3-(5-methyl-furan-2-yl)-propionamide |
| 20 | 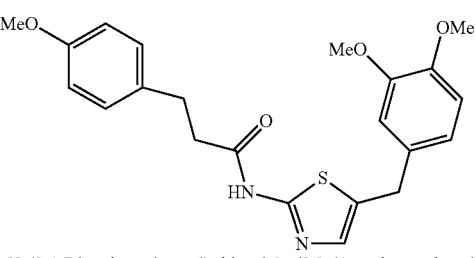
N-[5-(3,4-Dimethoxy-benzyl)-thiazol-2-yl]-3-(4-methoxy-phenyl)-propionamide |
| 21 | 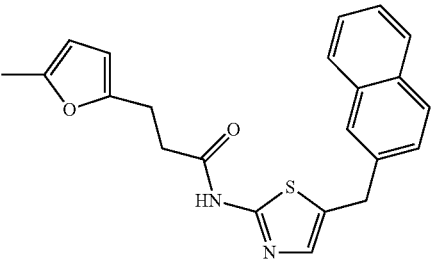 [SMILES: Cc1ccc(CCC(=O)Nc2ncc(Cc3ccc4ccccc4c3)s2)o1]
3-(5-Methyl-furan-2-yl)-N-(5-naphthalen-2-ylmethyl-thiazol-2-yl)-propionamide |
| 22 | 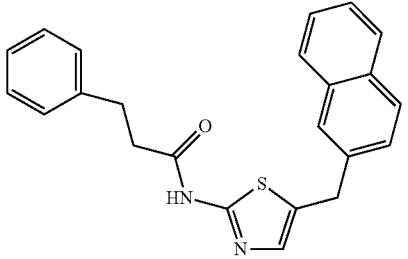 [SMILES: O=C(CCc1ccccc1)Nc1ncc(Cc2ccc3ccccc3c2)s1]
N-(5-Naphthalen-2-ylmethyl-thiazol-2-yl)-3-phenyl-propionamide |
| 23 | 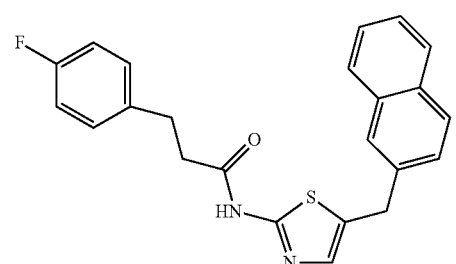
3-(4-Fluoro-phenyl)-N-(5-naphthalen-2-ylmethyl-thiazol-2-yl)-propionamide |

TABLE 1-continued
| Compd ID | Structure |
|---|---|
| 24 | 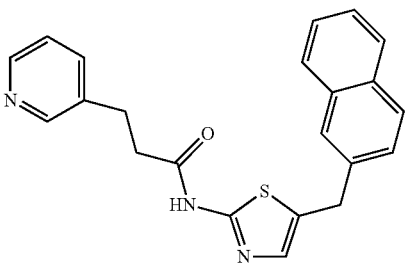 [SMILES: O=C(CCc1cccnc1)Nc1ncc(Cc2ccc3ccccc3c2)s1]<br>N-(5-Naphthalen-2-ylmethyl-thiazol-2-yl)-3-pyridin-3-yl-propionamide |
| 25 | 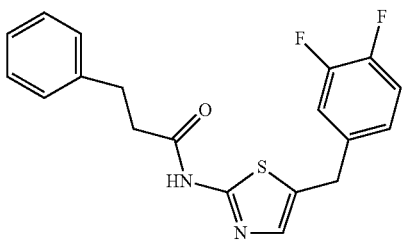 [SMILES: O=C(CCc1ccccc1)Nc1ncc(Cc2ccc(F)c(F)c2)s1]<br>N-[5-(3,4-Difluoro-benzyl)-thiazol-2-yl]-3-phenyl-propionamide |
| 26 | <br>N-[5-(3,4-Difluoro-benzyl)-thiazol-2-yl]-3-(3-methoxy-phenyl)-propionamide |
| 27 | 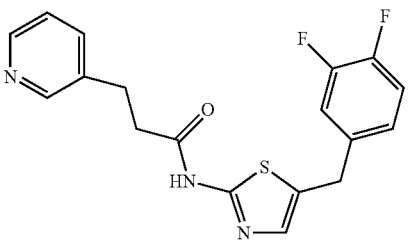 [SMILES: O=C(CCc1cccnc1)Nc1ncc(Cc2ccc(F)c(F)c2)s1]<br>N-[5-(3,4-Difluoro-benzyl)-thiazol-2-yl]-3-pyridin-3-yl-propionamide |
| 28 | 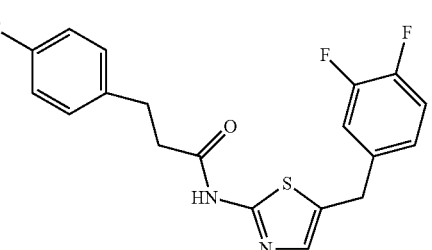<br>N-[5-(3,4-Difluoro-benzyl)-thiazol-2-yl]-3-(4-fluoro-phenyl)-propionamide |

TABLE 1-continued
| Compd ID | Structure |
|---|---|
| 29 | 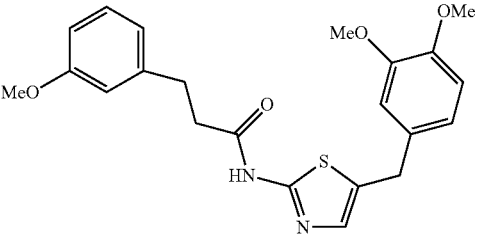 [SMILES: COc1cccc(CCC(=O)Nc2ncc(Cc3ccc(OC)c(OC)c3)s2)c1]<br>N-[5-(3,4-Dimethoxy-benzyl)-thiazol-2-yl]-3-(3-methoxy-phenyl)-propionamide |
| 30 | 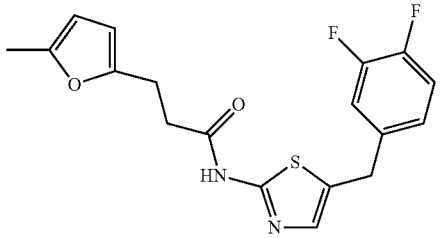 [SMILES: Cc1ccc(CCC(=O)Nc2ncc(Cc3ccc(F)c(F)c3)s2)o1]<br>N-[5-(3,4-Difluoro-benzyl)-thiazol-2-yl]-3-(5-methyl-furan-2-yl)-propionamide |
| 31 | 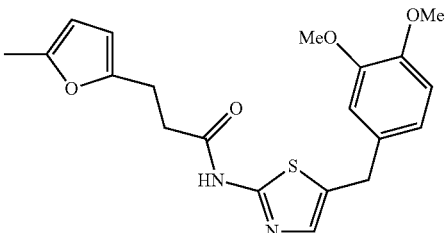<br>N-[5-(3,4-Dimethoxy-benzyl)-thiazol-2-yl]-3-(5-methyl-furan-2-yl)-propionamide |
| 32 | 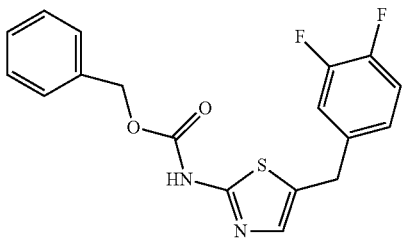 [SMILES: O=C(Nc1ncc(Cc2ccc(F)c(F)c2)s1)OCc1ccccc1]<br>[5-(3,4-Difluoro-benzyl)-thiazol-2-yl]-carbamic acid benzyl ester |
| 33 | 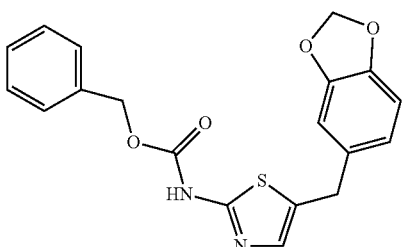<br>(5-Benzo[1,3]dioxol-5-ylmethyl-thiazol-2-yl)-carbamic acid benzyl ester |

TABLE 1-continued

| Compd ID | Structure |
|---|---|
| 34 | 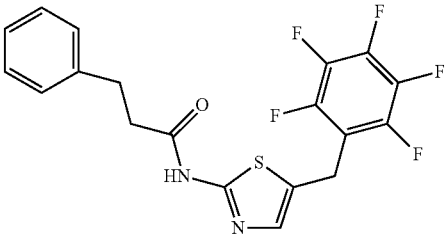 [SMILES: O=C(CCc1ccccc1)Nc1ncc(Cc2c(F)c(F)c(F)c(F)c2F)s1]<br>N-(5-Pentafluorophenylmethyl-thiazol-2-yl)-3-phenyl-propionamide |
| 35 | 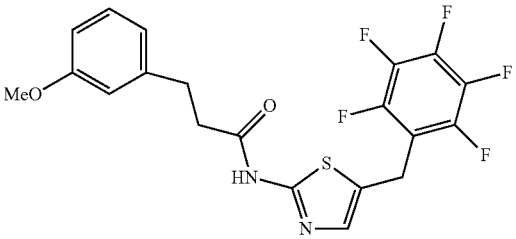 [SMILES: COc1cccc(CCC(=O)Nc2ncc(Cc3c(F)c(F)c(F)c(F)c3F)s2)c1]<br>3-(3-Methoxy-phenyl)-N-(5-pentafluorophenylmethyl-thiazol-2-yl)-propionamide |
| 36 | 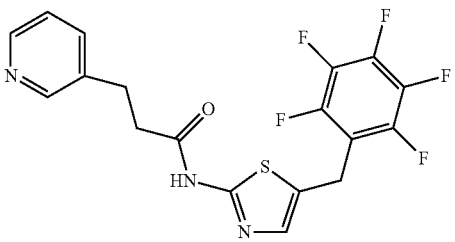 [SMILES: O=C(CCc1cccnc1)Nc1ncc(Cc2c(F)c(F)c(F)c(F)c2F)s1]<br>N-(5-Pentafluorophenylmethyl-thiazol-2-yl)-3-pyridin-3-yl-propionamide |
| 37 | 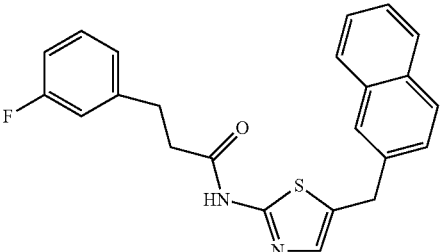<br>3-(3-Fluoro-phenyl)-N-(5-naphthalen-2-ylmethyl-thiazol-2-yl)-propionamide |
| 38 | 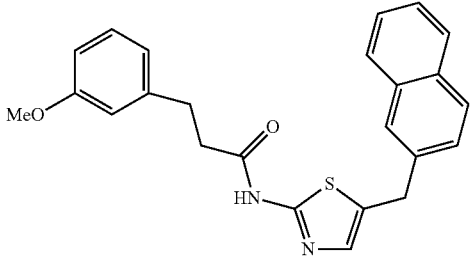 [SMILES: COc1cccc(CCC(=O)Nc2ncc(Cc3ccc4ccccc4c3)s2)c1]<br>3-(3-Methoxy-phenyl)-N-(5-naphthalen-2-ylmethyl-thiazol-2-yl)-propionamide |

TABLE 1-continued

| Compd ID | Structure |
|---|---|
| 39 | 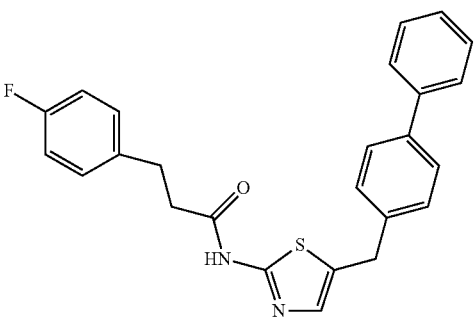 [SMILES: O=C(CCc1ccc(F)cc1)Nc1ncc(Cc2ccc(-c3ccccc3)cc2)s1]<br>N-(5-Biphenyl-4-ylmethyl-thiazol-2-yl)-3-(4-fluoro-phenyl)-propionamide |
| 40 | 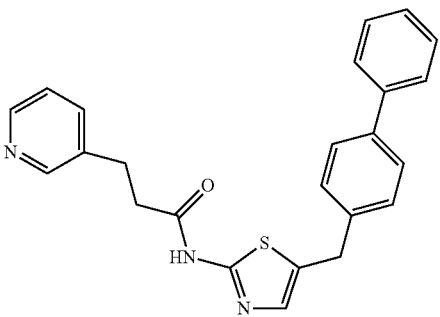 [SMILES: O=C(CCc1cccnc1)Nc1ncc(Cc2ccc(-c3ccccc3)cc2)s1]<br>N-(5-Biphenyl-4-ylmethyl-thiazol-2-yl)-3-pyridin-3-yl-propionamide |
| 41 | 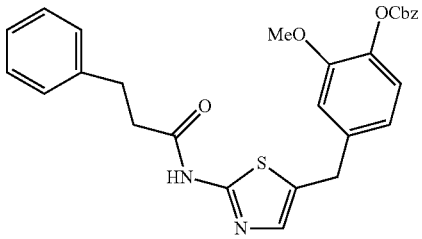<br>Carbonic acid benzyl ester 2-methoxy-4-[2-(3-phenyl-propionylamino)-thiazol-5-ylmethyl]-phenyl ester |
| 42 | 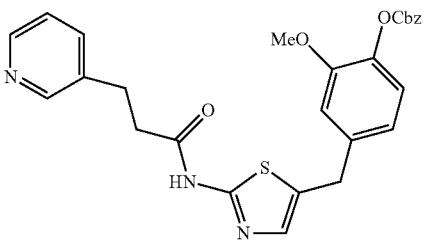<br>Carbonic acid benzyl ester 2-methoxy-4-[2-(3-pyridin-3-yl-propionylamino)-thiazol-5-ylmethyl]-phenyl ester |
| 43 | 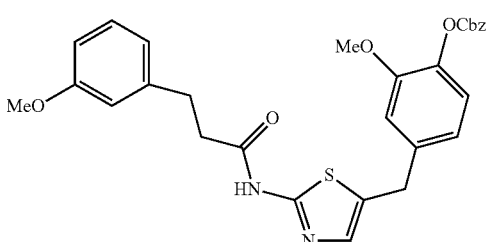<br>Carbonic acid benzyl ester 2-methoxy-4-{2-[3-(3-methoxy-phenyl)-propionylamino]-thiazol-5-ylmethyl}-phenyl ester |

TABLE 1-continued

| Compd ID | Structure |
|---|---|
| 44 | 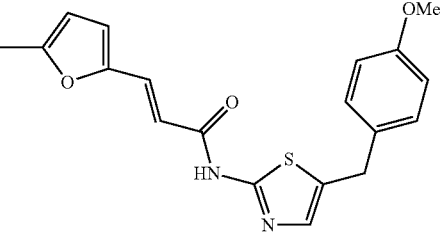 [SMILES: COc1ccc(Cc2cnc(NC(=O)/C=C/c3ccc(C)o3)s2)cc1]<br>N-[5-(4-Methoxy-benzyl)-thiazol-2-yl]-3-(5-methyl-furan-2-yl)-acrylamide |
| 45 | 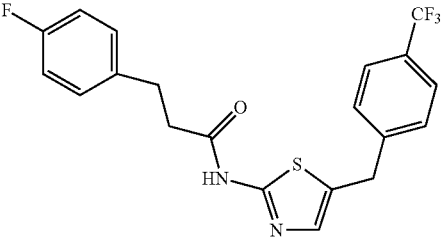 [SMILES: O=C(CCc1ccc(F)cc1)Nc1ncc(Cc2ccc(C(F)(F)F)cc2)s1]<br>3-(4-Fluoro-phenyl)-N-[5-(4-trifluoromethyl-benzyl)-thiazol-2-yl]-propionamide |
| 46 | 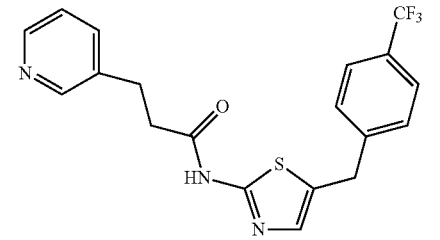 [SMILES: O=C(CCc1cccnc1)Nc1ncc(Cc2ccc(C(F)(F)F)cc2)s1]<br>3-Pyridin-3-yl-N-[5-(4-trifluoromethyl-benzyl)-thiazol-2-yl]-propionamide |
| 47 | 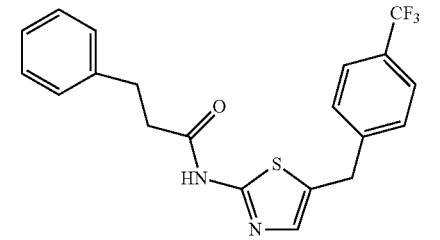 [SMILES: O=C(CCc1ccccc1)Nc1ncc(Cc2ccc(C(F)(F)F)cc2)s1]<br>3-Phenyl-N-[5-(4-trifluoromethyl-benzyl)-thiazol-2-yl]-propionamide |
| 48 | 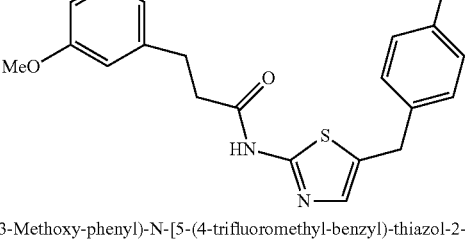<br>3-(3-Methoxy-phenyl)-N-[5-(4-trifluoromethyl-benzyl)-thiazol-2-yl]-propionamide |

TABLE 1-continued
| Compd ID | Structure |
|---|---|
| 49 | 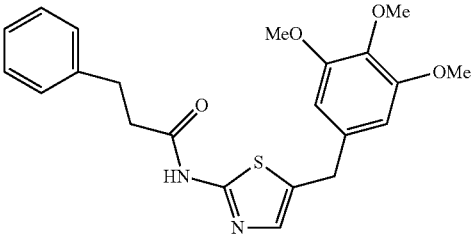 [SMILES: COc1cc(Cc2cnc(NC(=O)CCc3ccccc3)s2)cc(OC)c1OC]<br>3-Phenyl-N-[5-(3,4,5-trimethoxy-benzyl)-thiazol-2-yl]-propionamide |
| 50 | 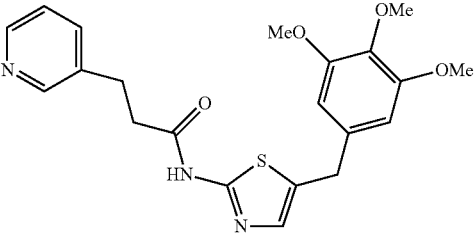 [SMILES: COc1cc(Cc2cnc(NC(=O)CCc3cccnc3)s2)cc(OC)c1OC]<br>3-Pyridin-3-yl-N-[5-(3,4,5-trimethoxy-benzyl)-thiazol-2-yl]-propionamide |
| 51 | 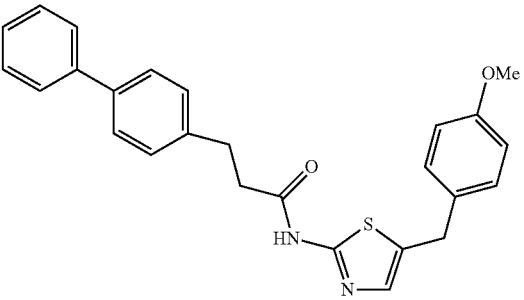 [SMILES: COc1ccc(Cc2cnc(NC(=O)CCc3ccc(-c4ccccc4)cc3)s2)cc1]<br>3-Biphenyl-4-yl-N-[5-(4-methoxy-benzyl)-thiazol-2-yl]-propionamide |
| 52 | 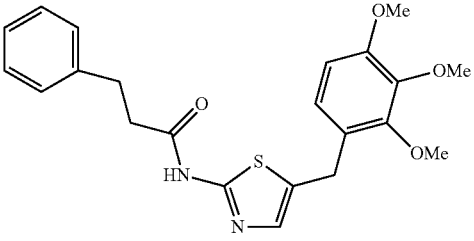 [SMILES: COc1ccc(Cc2cnc(NC(=O)CCc3ccccc3)s2)c(OC)c1OC]<br>3-Phenyl-N-[5-(2,3,4-trimethoxy-benzyl)-thiazol-2-yl]-propionamide |
| 53 | 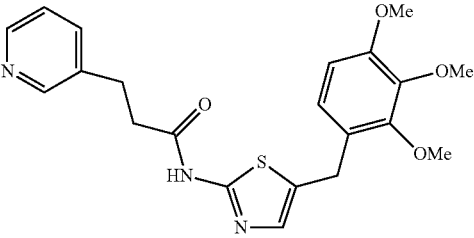 [SMILES: COc1ccc(Cc2cnc(NC(=O)CCc3cccnc3)s2)c(OC)c1OC]<br>3-Pyridin-3-yl-N-[5-(2,3,4-trimethoxy-benzyl)-thiazol-2-yl]-propionamide |

TABLE 1-continued
| Compd ID | Structure |
|---|---|
| 54 | 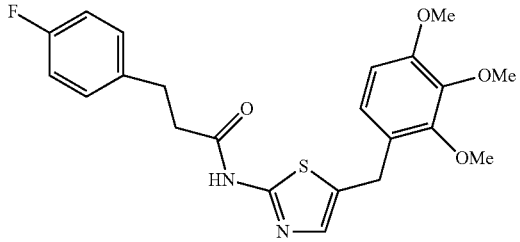 [SMILES: COc1ccc(Cc2cnc(NC(=O)CCc3ccc(F)cc3)s2)c(OC)c1OC]<br>3-(4-Fluoro-phenyl)-N-[5-(2,3,4-trimethoxy-benzyl)-thiazol-2-yl]-propionamide |
| 55 | 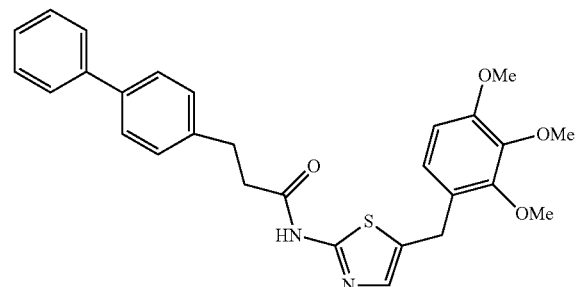 [SMILES: COc1ccc(Cc2cnc(NC(=O)CCc3ccc(-c4ccccc4)cc3)s2)c(OC)c1OC]<br>3-Biphenyl-4-yl-N-[5-(2,3,4-trimethoxy-benzyl)-thiazol-2-yl]-propionamide |
| 56 | 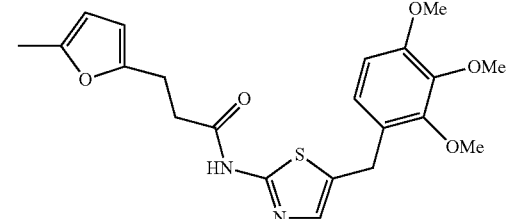<br>3-(5-Methyl-furan-2-yl)-N-[5-(2,3,4-trimethoxy-benzyl)-thiazol-2-yl]-propionamide |
| 57 | 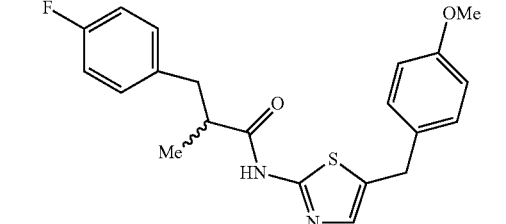<br>3-(4-Fluoro-phenyl)-N-[5-(4-methoxy-benzyl)-thiazol-2-yl]-2-methyl-propionamide |
| 58 | 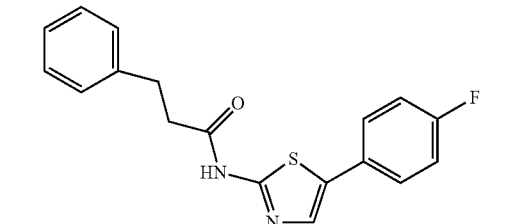<br>N-[5-(4-Fluoro-phenyl)-thiazol-2-yl]-3-phenyl-propionamide |

TABLE 1-continued
| Compd ID | Structure |
|---|---|
| 59 | 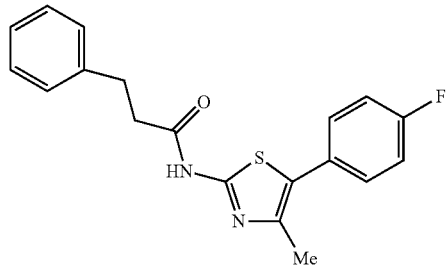 [SMILES: Cc1nc(NC(=O)CCc2ccccc2)sc1-c1ccc(F)cc1]
N-[5-(4-Fluoro-phenyl)-4-methyl-thiazol-2-yl]-3-phenyl-propionamide |
| 60 | 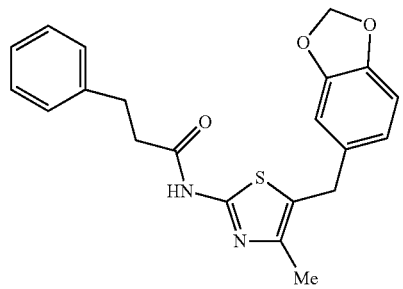 [SMILES: Cc1nc(NC(=O)CCc2ccccc2)sc1Cc1ccc2c(c1)OCO2]
N-(5-Benzo[1,3]dioxol-5-ylmethyl-4-methyl-thiazol-2-yl)-3-phenyl-propionamide |
| 61 | 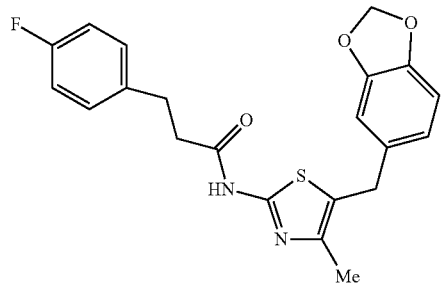 [SMILES: Cc1nc(NC(=O)CCc2ccc(F)cc2)sc1Cc1ccc2c(c1)OCO2]
N-(5-Benzo[1,3]dioxol-5-ylmethyl-4-methyl-thiazol-2-yl)-3-(4-fluoro-phenyl)-propionamide |
| 62 | 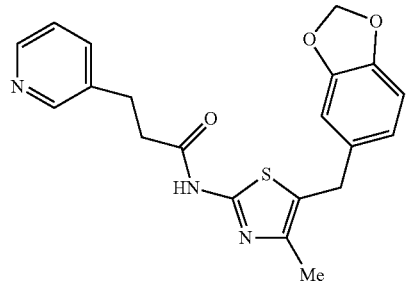 [SMILES: Cc1nc(NC(=O)CCc2cccnc2)sc1Cc1ccc2c(c1)OCO2]
N-(5-Benzo[1,3]dioxol-5-ylmethyl-4-methyl-thiazol-2-yl)-3-pyridin-3-yl-propionamide |

TABLE 1-continued

| Compd ID | Structure |
|---|---|
| 63 | N-(5-Benzo[1,3]dioxol-5-ylmethyl-4-methyl-thiazol-2-yl)-3-(3-methoxy-phenyl)-propionamide |
| 64 | N-[5-(4-Fluoro-phenoxy)-thiazol-2-yl]-3-(5-methyl-furan-2-yl)-propionamide |
| 65 | 3-(4-Fluoro-phenyl)-N-(5-phenylsulfanyl-thiazol-2-yl)-propionamide |
| 66 | N-(5-Phenylsulfanyl-thiazol-2-yl)-3-pyridin-3-yl-propionamide |
| 67 | 3-Phenyl-N-(5-phenylsulfanyl-thiazol-2-yl)-propionamide |

TABLE 1-continued

| Compd ID | Structure |
|---|---|
| 68 | 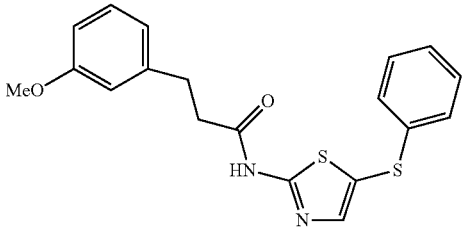 [SMILES: COc1cccc(CCC(=O)Nc2ncc(Sc3ccccc3)s2)c1]<br>3-(3-Methoxy-phenyl)-N-(5-phenylsulfanyl-thiazol-2-yl)-propionamide |
| 69 | 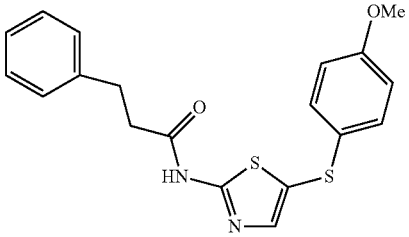 [SMILES: COc1ccc(Sc2cnc(NC(=O)CCc3ccccc3)s2)cc1]<br>N-[5-(4-Methoxy-phenylsulfanyl)-thiazol-2-yl]-3-phenyl-propionamide |
| 70 | 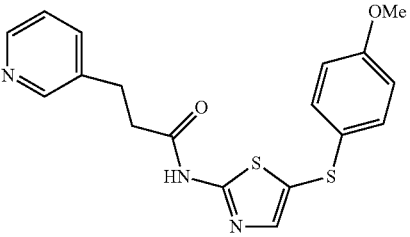 [SMILES: COc1ccc(Sc2cnc(NC(=O)CCc3cccnc3)s2)cc1]<br>N-[5-(4-Methoxy-phenylsulfanyl)-thiazol-2-yl]-3-pyridin-3-yl-propionamide |
| 71 | 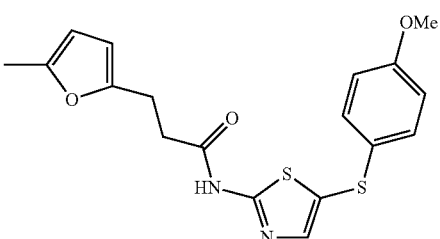<br>N-[5-(4-Methoxy-phenylsulfanyl)-thiazol-2-yl]-3-(5-methyl-furan-2-yl)-propionamide |
| 72 | 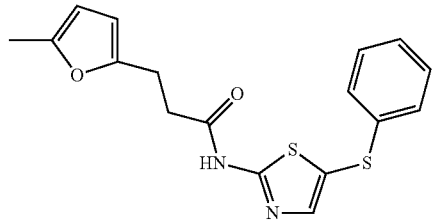 [SMILES: Cc1ccc(CCC(=O)Nc2ncc(Sc3ccccc3)s2)o1]<br>3-(5-Methyl-furan-2-yl)-N-(5-phenylsulfanyl-thiazol-2-yl)-propionamide |

TABLE 1-continued

| Compd ID | Structure |
|---|---|
| 73 | 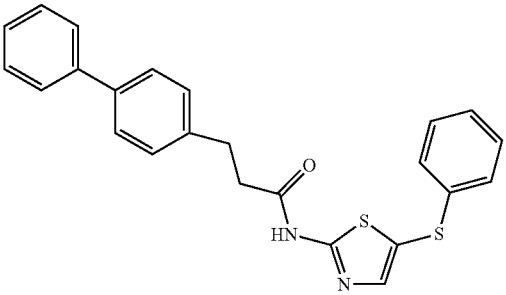 [SMILES: O=C(CCc1ccc(-c2ccccc2)cc1)Nc1ncc(Sc2ccccc2)s1]<br>3-Biphenyl-4-yl-N-(5-phenylsulfanyl-thiazol-2-yl)-propionamide |
| 74 | 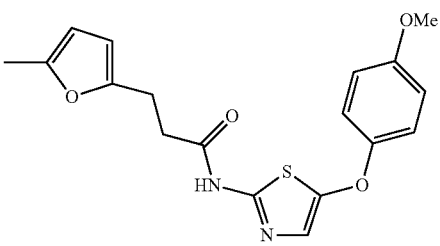<br>N-[5-(4-Methoxy-phenoxy)-thiazol-2-yl]-3-(5-methyl-furan-2-yl)-propionamide |
| 75 | 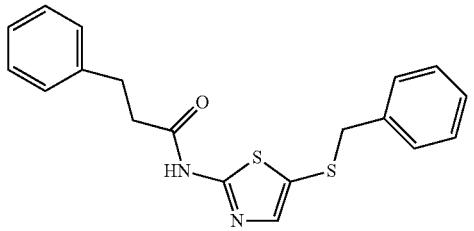 [SMILES: O=C(CCc1ccccc1)Nc1ncc(SCc2ccccc2)s1]<br>N-(5-Benzylsulfanyl-thiazol-2-yl)-3-phenyl-propionamide |
| 76 | 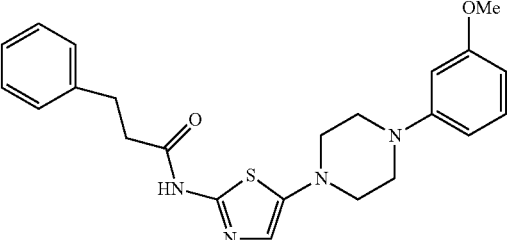<br>N-{5-[4-(3-Methoxy-phenyl)-piperazin-1-yl]-thiazol-2-yl}-3-phenyl-propionamide |
| 77 | 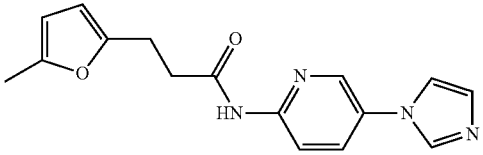 [SMILES: Cc1ccc(CCC(=O)Nc2ccc(-n3ccnc3)cn2)o1]<br>N-(5-Imidazol-1-yl-pyridin-2-yl)-3-(5-methyl-furan-2-yl)-propionamide |
| 78 | 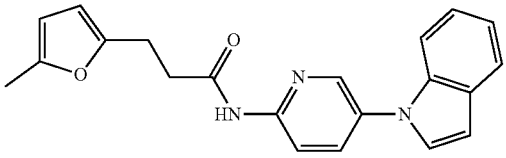 [SMILES: Cc1ccc(CCC(=O)Nc2ccc(-n3ccc4ccccc43)cn2)o1]<br>N-(5-Indol-1-yl-pyridin-2-yl)-3-(5-methyl-furan-2-yl)-propionamide |

TABLE 1-continued

| Compd ID | Structure |
|---|---|
| 79 | 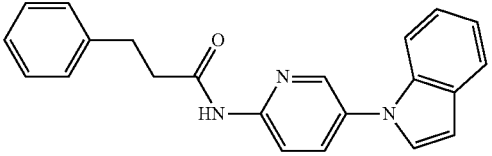 [SMILES: O=C(CCc1ccccc1)Nc1ccc(-n2ccc3ccccc32)cn1]<br>N-(5-Indol-1-yl-pyridin-2-yl)-3-phenyl-propionamide |
| 80 | 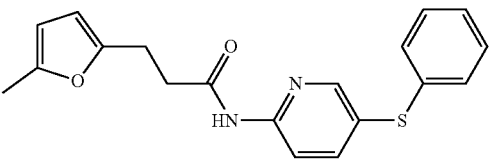 [SMILES: Cc1ccc(CCC(=O)Nc2ccc(Sc3ccccc3)cn2)o1]<br>3-(5-Methyl-furan-2-yl)-N-(5-phenylsulfanyl-pyridin-2-yl)-propionamide |
| 81 | 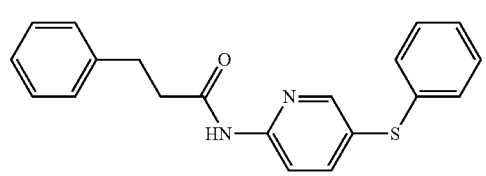 [SMILES: O=C(CCc1ccccc1)Nc1ccc(Sc2ccccc2)cn1]<br>3-Phenyl-N-(5-phenylsulfanyl-pyridin-2-yl)-propionamide |
| 82 | 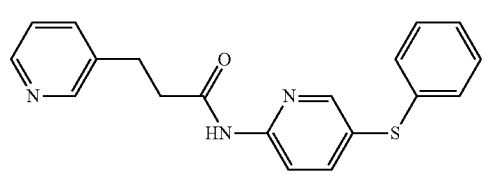 [SMILES: O=C(CCc1cccnc1)Nc1ccc(Sc2ccccc2)cn1]<br>N-(5-Phenylsulfanyl-pyridin-2-yl)-3-pyridin-3-yl-propionamide |
| 83 | 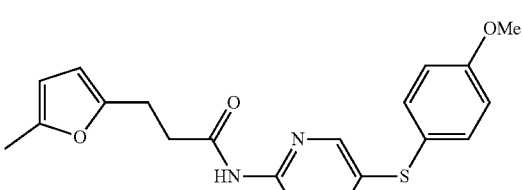<br>N-[5-(4-Methoxy-phenylsulfanyl)-pyridin-2-yl]-3-(5-methyl-furan-2-yl)-propionamide |
| 84 | 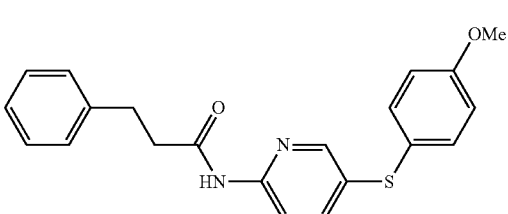<br>N-[5-(4-Methoxy-phenylsulfanyl)-pyridin-2-yl]-3-phenyl-propionamide |
| 85 | 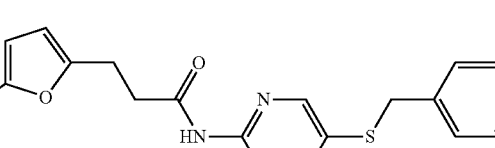<br>N-(5-Benzylsulfanyl-pyridin-2-yl)-3-(5-methyl-furan-2-yl)-propionamide |

TABLE 1-continued

| Compd ID | Structure |
|---|---|
| 86 | 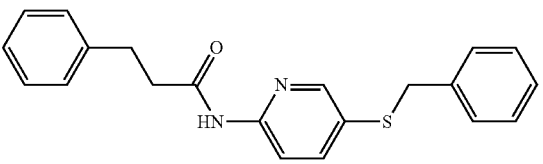 [SMILES: O=C(CCc1ccccc1)Nc1ccc(SCc2ccccc2)cn1]<br>N-(5-Benzylsulfanyl-pyridin-2-yl)-3-phenyl-propionamide |
| 87 | 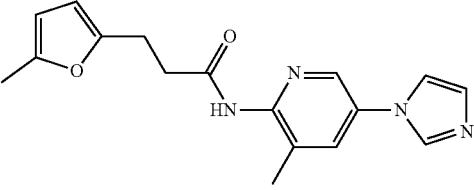 [SMILES: Cc1ccc(CCC(=O)Nc2ncc(-n3ccnc3)cc2C)o1]<br>N-(5-Imidazol-1-yl-3-methyl-pyridin-2-yl)-3-(5-methyl-furan-2-yl)-propionamide |
| 88 | 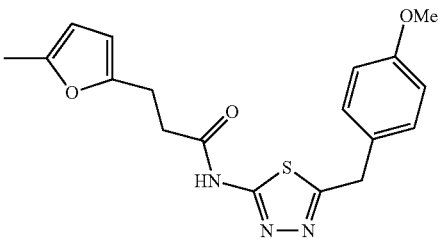 [SMILES: COc1ccc(Cc2nnc(NC(=O)CCc3ccc(C)o3)s2)cc1]<br>N-[5-(4-Methoxy-benzyl)-[1,3,4]thiadiazol-2-yl]-3-(5-methyl-furan-2-yl)-propionamide |
| 89 | 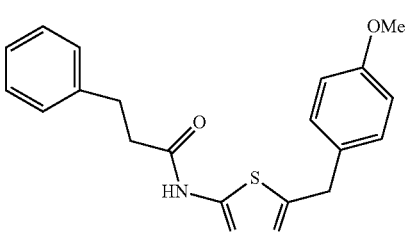<br>N-[5-(4-Methoxy-benzyl)-[1,3,4]thiadiazol-2-yl]-3-phenyl-propionamide |
| 90 | 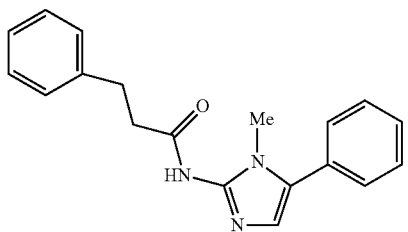 [SMILES: Cn1c(-c2ccccc2)cnc1NC(=O)CCc1ccccc1]<br>N-(1-Methyl-5-phenyl-1H-imidazol-2-yl)-3-phenyl-propionamide |
| 91 | 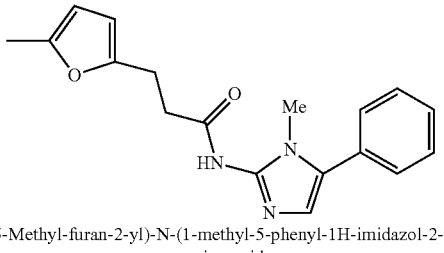<br>3-(5-Methyl-furan-2-yl)-N-(1-methyl-5-phenyl-1H-imidazol-2-yl)-propionamide |

TABLE 1-continued

| Compd ID | Structure |
|---|---|
| 92 | 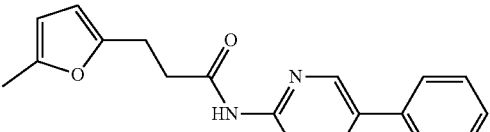 3-(5-Methyl-furan-2-yl)-N-(5-phenyl-pyrimidin-2-yl)-propionamide |
| 93 | 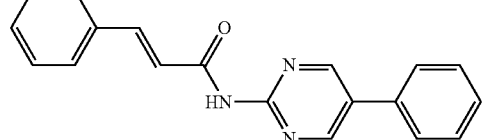 3-Phenyl-N-(5-phenyl-pyrimidin-2-yl)-acrylamide |
| 94 | 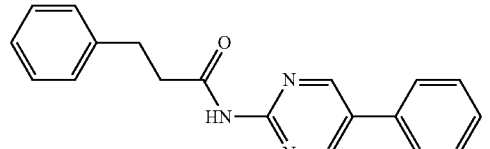 3-Phenyl-N-(5-phenyl-pyrimidin-2-yl)-propionamide |
| 95 | 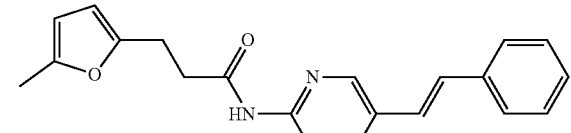 3-(5-Methyl-furan-2-yl)-N-(5-styryl-pyrimidin-2-yl)-propionamide |
| 96 | 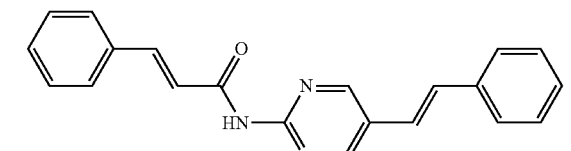 3-Phenyl-N-(5-styryl-pyrimidin-2-yl)-acrylamide |
| 97 | 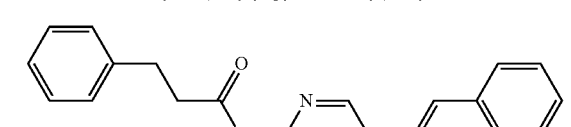 3-Phenyl-N-(5-styryl-pyrimidin-2-yl)-propionamide |
| 98 | 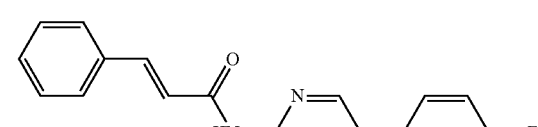 N-[5-(4-Fluoro-phenyl)-pyrimidin-2-yl]-3-phenyl-acrylamide |
| 99 | 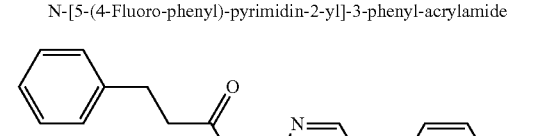 N-[5-(4-Fluoro-phenyl)-pyrimidin-2-yl]-3-phenyl-propionamide |

TABLE 1-continued

| Compd ID | Structure |
|---|---|
| 100 | 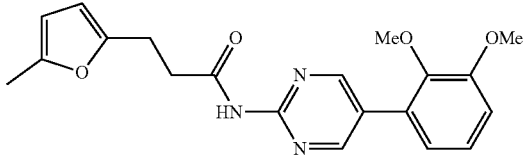 [SMILES: COc1cccc(-c2cnc(NC(=O)CCc3ccc(C)o3)nc2)c1OC]

N-[5-(2,3-Dimethoxy-phenyl)-pyrimidin-2-yl]-3-(5-methyl-furan-2-yl)-propionamide |
| 101 | 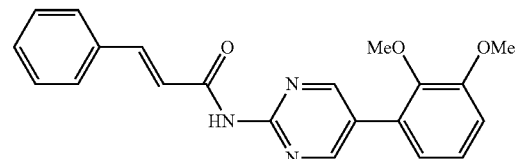

N-[5-(2,3-Dimethoxy-phenyl)-pyrimidin-2-yl]-3-phenyl-acrylamide |
| 102 | 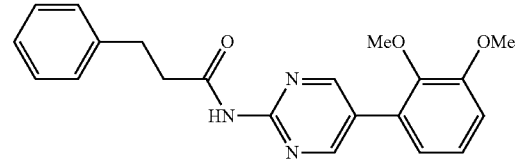 [SMILES: COc1cccc(-c2cnc(NC(=O)CCc3ccccc3)nc2)c1OC]

N-[5-(2,3-Dimethoxy-phenyl)-pyrimidin-2-yl]-3-phenyl-propionamide |
| 103 | 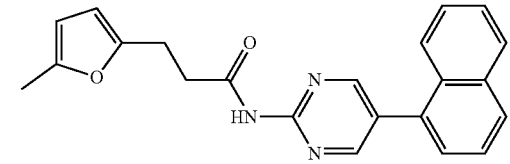 [SMILES: Cc1ccc(CCC(=O)Nc2ncc(-c3cccc4ccccc34)cn2)o1]

3-(5-Methyl-furan-2-yl)-N-(5-naphthalen-1-yl-pyrimidin-2-yl)-propionamide |
| 104 | 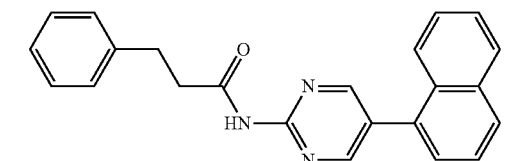

N-(5-Naphthalen-1-yl-pyrimidin-2-yl)-3-phenyl-propionamide |
| 105 | 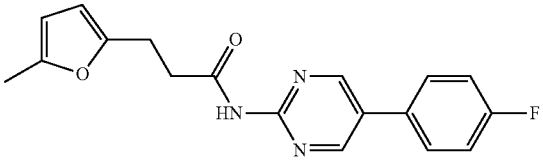 [SMILES: Cc1ccc(CCC(=O)Nc2ncc(-c3ccc(F)cc3)cn2)o1]

N-[5-(4-Fluoro-phenyl)-pyrimidin-2-yl]-3-(5-methyl-furan-2-yl)-propionamide |
| 106 | 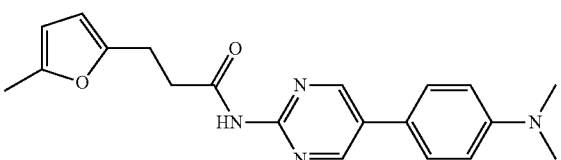

N-[5-(4-Dimethylamino-phenyl)-pyrimidin-2-yl]-3-(5-methyl-furan-2-yl)-propionamide |

TABLE 1-continued

| Compd ID | Structure |
|---|---|
| 107 | 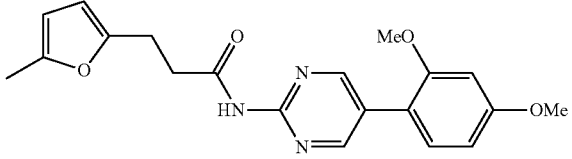 [SMILES: COc1ccc(-c2cnc(NC(=O)CCc3ccc(C)o3)nc2)c(OC)c1]<br>N-[5-(2,4-Dimethoxy-phenyl)-pyrimidin-2-yl]-3-(5-methyl-furan-2-yl)-propionamide |
| 108 | 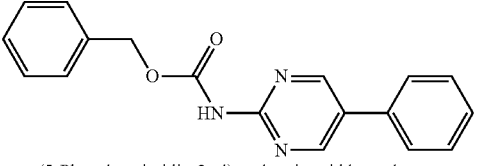<br>(5-Phenyl-pyrimidin-2-yl)-carbamic acid benzyl ester |
| 109 | 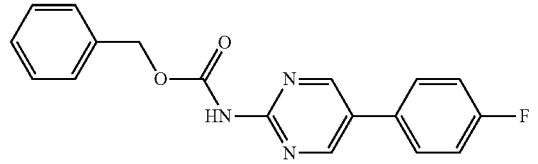 [SMILES: O=C(Nc1ncc(-c2ccc(F)cc2)cn1)OCc1ccccc1]<br>[5-(4-Fluoro-phenyl)-pyrimidin-2-yl]-carbamic acid benzyl ester |
| 110 | 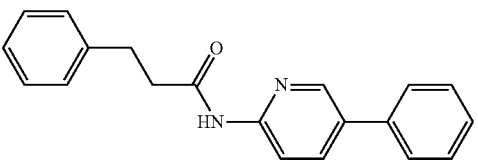 [SMILES: O=C(CCc1ccccc1)Nc1ccc(-c2ccccc2)cn1]<br>3-Phenyl-N-(5-phenyl-pyridin-2-yl)-propionamide |
| 111 | 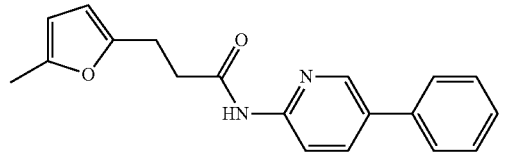 [SMILES: Cc1ccc(CCC(=O)Nc2ccc(-c3ccccc3)cn2)o1]<br>3-(5-Methyl-furan-2-yl)-N-(5-phenyl-pyridin-2-yl)-propionamide |
| 112 | 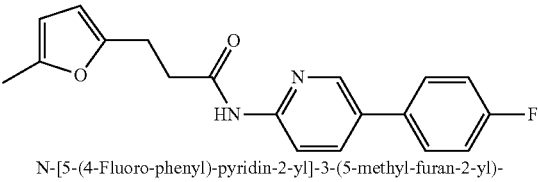<br>N-[5-(4-Fluoro-phenyl)-pyridin-2-yl]-3-(5-methyl-furan-2-yl)-propionamide |
| 113 | 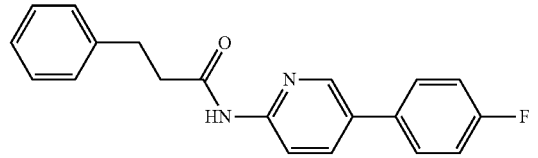 [SMILES: O=C(CCc1ccccc1)Nc1ccc(-c2ccc(F)cc2)cn1]<br>N-[5-(4-Fluoro-phenyl)-pyridin-2-yl]-3-phenyl-propionamide |
| 114 | 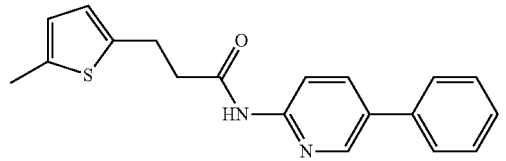 [SMILES: Cc1ccc(CCC(=O)Nc2ccc(-c3ccccc3)cn2)s1]<br>3-(5-Methyl-thiophen-2-yl)-N-(5-phenyl-pyridin-2-yl)-propionamide |

TABLE 1-continued

| Compd ID | Structure |
|---|---|
| 115 | 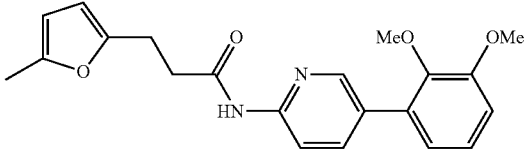 [SMILES: COc1cccc(-c2ccc(NC(=O)CCc3ccc(C)o3)nc2)c1OC] N-[5-(2,3-Dimethoxy-phenyl)-pyridin-2-yl]-3-(5-methyl-furan-2-yl)-propionamide |
| 116 | 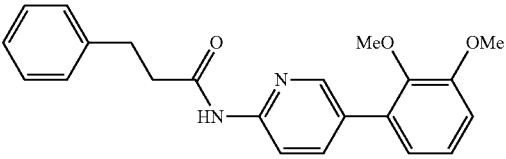 [SMILES: COc1cccc(-c2ccc(NC(=O)CCc3ccccc3)nc2)c1OC] N-[5-(2,3-Dimethoxy-phenyl)-pyridin-2-yl]-3-phenyl-propionamide |
| 117 | 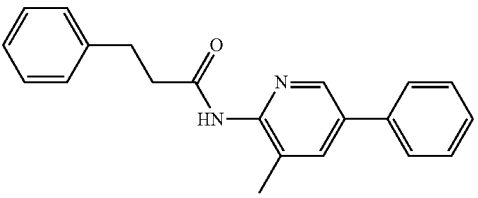 [SMILES: Cc1cc(-c2ccccc2)cnc1NC(=O)CCc1ccccc1] N-(3-Methyl-5-phenyl-pyridin-2-yl)-3-phenyl-propionamide |
| 118 | 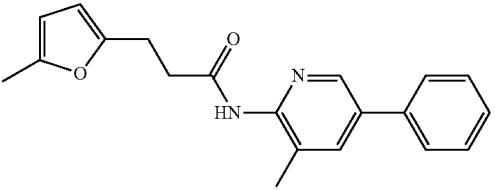 [SMILES: Cc1ccc(CCC(=O)Nc2ncc(-c3ccccc3)cc2C)o1] 3-(5-Methyl-furan-2-yl)-N-(3-methyl-5-phenyl-pyridin-2-yl)-propionamide |
| 119 | 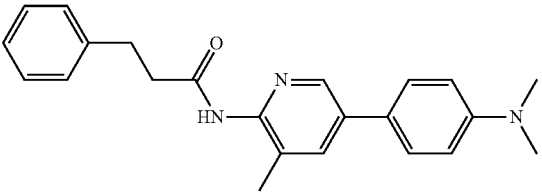 [SMILES: Cc1cc(-c2ccc(N(C)C)cc2)cnc1NC(=O)CCc1ccccc1] N-[5-(4-Dimethylamino-phenyl)-3-methyl-pyridin-2-yl]-3-phenyl-propionamide |
| 120 | 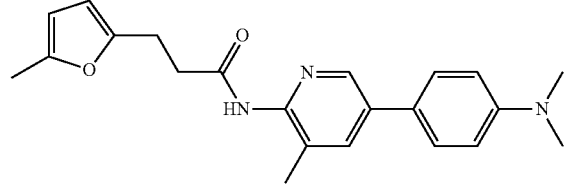 N-[5-(4-Dimethylamino-phenyl)-3-methyl-pyridin-2-yl]-3-(5-methyl-furan-2-yl)-propionamide |

TABLE 1-continued

| Compd ID | Structure |
|---|---|
| 121 | 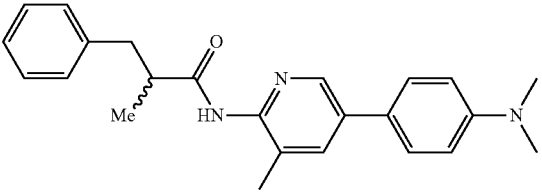 [SMILES: Cc1cc(-c2ccc(N(C)C)cc2)cnc1NC(=O)C(C)Cc1ccccc1]
N-[5-(4-Dimethylamino-phenyl)-3-methyl-pyridin-2-yl]-2-methyl-3-phenyl-propionamide |
| 122 | 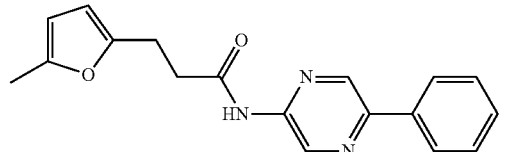
3-(5-Methyl-furan-2-yl)-N-(5-phenyl-pyrazin-2-yl)-propionamide |
| 123 | 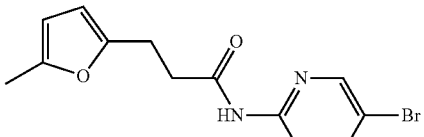
N-(5-Bromo-pyridin-2-yl)-3-(5-methyl-furan-2-yl)-propionamide |
| 124 | 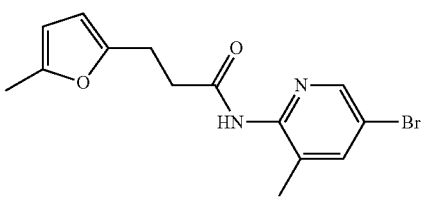 [SMILES: Cc1ccc(CCC(=O)Nc2ncc(Br)cc2C)o1]
N-(5-Bromo-3-methyl-pyridin-2-yl)-3-(5-methyl-furan-2-yl)-propionamide |

EXAMPLES

The following examples are presented to illustrated certain embodiments of the present invention, but should not be construed as limiting the scope of this invention.

Unless otherwise indicated, $^1$H NMR data were obtained at 500 MHz and the compounds of this invention demonstrated efficacy in the following assays as having $IC_{50}$ values of less than 10 µM. The abbreviations used herein are as follows, unless specified otherwise:

Bu butyl
Bn benzyl
BOC t-butyloxycarbonyl
BOP benzotriazol-1-yloxy tri/dimethylamino-phosphonium hexafluorophosphate
DCC dicyclohexylcarbodiimide
DMF N,N-dimethylformamide
DMAP 4-dimethylaminopyridine
EDC 1-(3-dimethylaminopropyl) 3-ethylcarbodiimide hydrochloride
EtOAc ethyl acetate
Eq. equivalent(s)
HOBt hydroxybenztriazole
LAH lithium aluminum hydride
MeOH methanol
MHz megahertz
MS (ES) mass spectrophotometer-electron spray
NMP N-methylpyrrolidinone
Ph phenyl
Pr propyl
TEA triethylamine
THF tetrandrofuran
TLC thin layer chromatography
Tetrakis tetrakis(triphenylphosphine)palladium Example 1

N-[5-(4-Methoxy-benzyl)-thiazol-2-yl]-3-phenyl-propionamide (9)

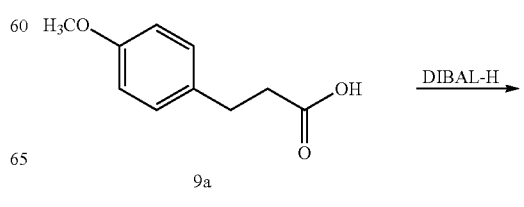

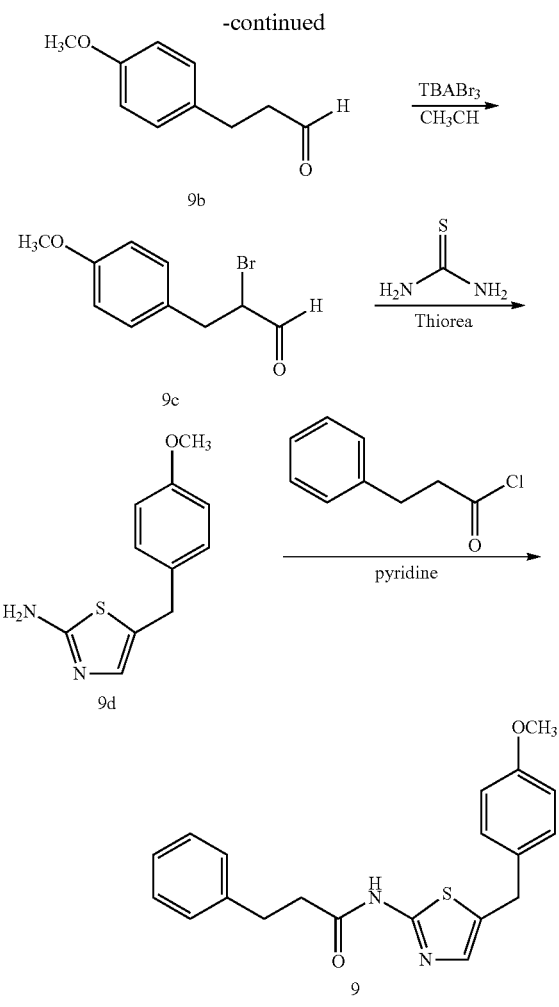

saturated aqueous NaHCO$_3$, dried over MgSO$_4$(s), and concentrated under reduced pressure. The residue was purified by column chromatography on silica gel to give 5-(4-methoxy-benzyl)-thiazol-2-ylamine (9d, 1.01 g, 4.54 mmol) as yellow solids in 75.2% yield.

A mixture of 5-(4-methoxy-benzyl)-thiazol-2-ylamine (9d, 1.0 g, 4.54 mmol) and 3-pyridin-3-yl-propionic acid (0.92 g, 5.45 mmol), EDCA (1.74 g, 9.08 mmol), HOBt (1.23 g, 9.08 mmol) and NEt3 (1.38 g, 13.6 mmol) in DMF (15.0 mL) was stirred for 16 hours. The reaction mixture was quenched with water and extracted with ethyl acetate. The organic layer was washed with saturated aqueous NaHCO$_3$, dried over MgSO$_4$(s), and concentrated under reduced pressure. The residue was purified by column chromatography on silica gel to give N-[5-(4-methoxy-benzyl)-thiazol-2-yl]-3-phenyl-propionamide (9, 1.05 g) in 66% yield: $^1$H NMR (500 MHz, CDCl$_3$) δ 7.27 (d, 2 H), 7.3-7.15 (m, 6 H), 6.86 (d, 2 H), 3.98 (s, 2 H), 3.72 (s, 3 H), 2.87 (m, 2 H), 2.64 (m, 2 H).

Example 2

Syntheses of compounds 1-63 listed in Table 1

Compounds 1-63 listed in Table 1 above were synthesized in a manner similar to that describe in Example 1. Their calculated mass and observed ESI-MS data are provided in Table 2.

TABLE 2

| Compd ID | Calculated Mass | Observed ESI-MS |
|---|---|---|
| 1 | 326.11 | 324.9 (M − H)$^+$ |
| 2 | 322.11 | 321.1 (M − H)$^+$ |
| 3 | 320.10 | 320.9 (M + H)$^+$ |
| 4 | 341.10 | 342.1 (M + H)$^+$ |
| 5 | 356.12 | 356.8 (M + H)$^+$ |
| 6 | 366.10 | 367.4 (M + H)$^+$ |
| 7 | 384.09 | 385.1 (M + H)$^+$ |
| 8 | 367.10 | 368.0 (M + H)$^+$ |
| 9 | 352.12 | 353.3 (M + H)$^+$ |
| 10 | 353.12 | 353.7 (M + H)$^+$ |
| 11 | 370.12 | 371.2 (M + H)$^+$ |
| 12 | 358.10 | 358.9 (M + H)$^+$ |
| 13 | 420.13 | 419.2 (M − H)$^+$ |
| 14 | 402.14 | 402.9 (M + H)$^+$ |
| 15 | 382.14 | 381.2 (M − H)$^+$ |
| 16 | 353.12 | 352.1 (M − H)$^+$ |
| 17 | 383.13 | 382.0 (M − H)$^+$ |
| 18 | 400.13 | 399.1 (M − H)$^+$ |
| 19 | 406.14 | 405.1 (M − H)$^+$ |
| 20 | 412.15 | 411.4 (M − H)$^+$ |
| 21 | 376.12 | 376.9 (M + H)$^+$ |
| 22 | 372.13 | 373.0 (M + H)$^+$ |
| 23 | 390.12 | 391.0 (M + H)$^+$ |
| 24 | 373.12 | 374.0 (M + H)$^+$ |
| 25 | 358.10 | 359.0 (M + H)$^+$ |
| 26 | 388.11 | 389.1 (M + H)$^+$ |
| 27 | 359.09 | 359.9 (M + H)$^+$ |
| 28 | 376.09 | 377.0 (M + H)$^+$ |
| 29 | 412.15 | 413.1 (M + H)$^+$ |
| 30 | 362.09 | 362.7 (M + H)$^+$ |
| 31 | 386.13 | 386.9 (M + H)$^+$ |
| 32 | 360.07 | 360.8 (M + H)$^+$ |
| 33 | 368.08 | 368.8 (M + H)$^+$ |
| 34 | 412.07 | 412.5 (M + H)$^+$ |
| 35 | 442.08 | 442.8 (M + H)$^+$ |
| 36 | 413.06 | 413.8 (M + H)$^+$ |
| 37 | 390.12 | 391.2 (M + H)$^+$ |
| 38 | 402.14 | 403.1 (M + H)$^+$ |
| 39 | 416.14 | 416.9 (M + H)$^+$ |
| 40 | 399.14 | 399.8 (M + H)$^+$ |
| 41 | 502.16 | 503.1 (M + H)$^+$ |
| 42 | 503.15 | 503.9 (M + H)$^+$ |

3-(4-Methoxy-phenyl)-propionic acid (9a, 1.80 g, 10.0 mmol) in toluene (25.0 mL) was cooled to −78° C. in dry ice-acetone bath for 5-10 minutes under N$_2$. DIBAL-H (11.0 mmol) was slowly added by syringe and stirred for 2 hours at −78° C. Then, the reaction mixture was poured quickly into an aqueous NH$_4$Cl solution with vigorous stirring. The solution was extracted twice with ether and the organic layer was washed with brine, dried over MgSO$_4$(s), and concentrated under reduced pressure. The residue was purified by column chromatography on silica gel to provide 3-(4-methoxy-phenyl)-propionaldehyde (9b, 1.16 g, 7.07 mmol) as yellow oil in 70.7% yield.

To a solution of 3-(4-Methoxy-phenyl)-propionaldehyde (9b, 1.00 g, 6.10 mmol) in acetonitrile (10.0 mL) was added TBABr$_3$ (1.00 g, 6.10 mmol). The reaction mixture was stirred at room temperature for 30 minutes and then quenched with water. The solution was concentrated under reduced pressure, and extracted with ethyl acetate. The organic layer was washed with brine, dried over MgSO$_4$(s), and concentrated under reduced pressure to give 2-bromo-3-(4-methoxy-phenyl)-propionaldehyde (9c), which was used directly for the next step without further purification.

A mixture of 2-bromo-3-(4-methoxy-phenyl)-propionaldehyde (9c) and thiourea (0.84 g, 11.0 mmol) in 95% EtOH (20.0 mL) was heated at reflux for 60 minutes. The solution was concentrated under reduced pressure and the residue was re-dissolved in ethyl acetate. The solution was washed with

TABLE 2-continued

| Compd ID | Calculated Mass | Observed ESI-MS |
| --- | --- | --- |
| 43 | 532.17 | 533.0 (M + H)+ |
| 44 | 354.10 | 354.6 (M + H)+ |
| 45 | 408.09 | 407.2 (M − H)+ |
| 46 | 391.10 | 391.8 (M + H)+ |
| 47 | 390.10 | 390.9 (M + H)+ |
| 48 | 420.11 | 420.7 (M + H)+ |
| 49 | 412.15 | 412.8 (M + H)+ |
| 50 | 413.14 | 413.9 (M + H)+ |
| 51 | 428.16 | 428.8 (M + H)+ |
| 52 | 412.15 | 412.8 (M + H)+ |
| 53 | 413.14 | 413.9 (M + H)+ |
| 54 | 430.14 | 430.8 (M + H)+ |
| 55 | 488.18 | 489.1 (M + H)+ |
| 56 | 416.14 | 416.9 (M + H)+ |
| 57 | 384.13 | 384.7 (M + H)+ |
| 58 | 326.09 | 325.0 (M − H)+ |
| 59 | 340.10 | 341.2 (M + H)+ |
| 60 | 380.12 | 381.2 (M + H)+ |
| 61 | 398.11 | 398.8 (M + H)+ |
| 62 | 381.11 | 382.1 (M + H)+ |
| 63 | 410.13 | 409.3 (M − H)+ |

Example 3

N-[5-(4-Methoxy-phenylsulfanyl)-thiazol-2-yl]-3-pyridin-3-yl-propionamide (70)

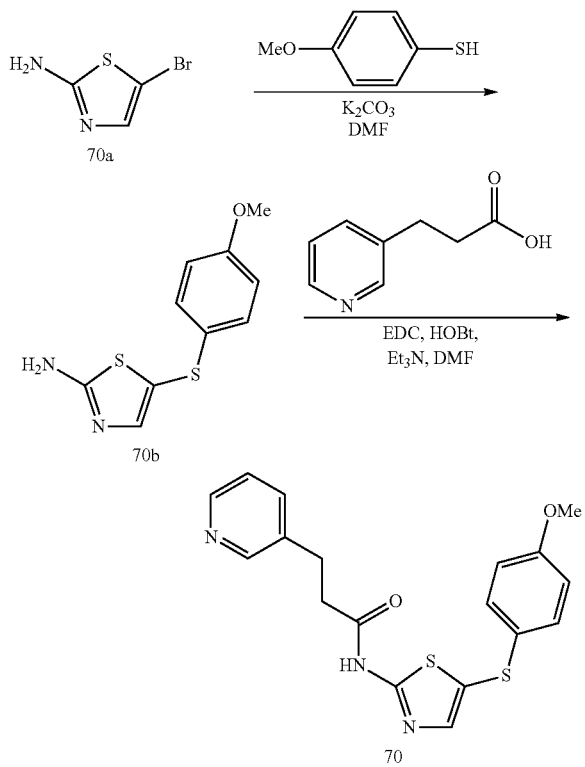

A solution of 5-bromo-thiazol-2-ylamine (70a, 10.0 g, 38.5 mmol), 4-methoxy-benzenethiol (4.70 ml, 38.5 mmol) and $K_2CO_3$ (21.0 g, 151 mmol) in DMF (100 mL) was heated at 80° C. for 1.0 hour and stirred further 16 hours at room temperature. The reaction mixture was quenched with water and extracted with ethyl acetate. The organic layer was washed with brine, dried over $MgSO_4(s)$, and concentrated under reduced pressure to give 5-(4-methoxy-phenylsulfanyl)-thiazol-2-ylamine (70b, 6.70 g).

A solution of 5-(4-methoxy-phenylsulfanyl)-thiazol-2-ylamine (70b, 3.0 g, 12.6 mmol), 3-pyridin-3-yl-propionic acid (2.30 g, 15.1 mmol), $NEt_3$ (6.10 ml, 44.1 mmol), EDC (4.80 g, 25.2 mmol) and HOBt (3.40 g, 25.2 mmol) in DMF (150 mL) was stirred at room temperature for 18 hours. The reaction mixture was quenched with water and extracted with ethyl acetate. The organic layer was washed with brine, dried over $MgSO_4(s)$, and concentrated under reduced pressure to give N-[5-(4-methoxy-phenylsulfanyl)-thiazol-2-yl]-3-pyridin-3-yl-propionamide (70, 3.50 g) in 75% yield: $^1H$ NMR (500 MHz, DMSO) δ 8.45 (d, 1H), 8.39 (m, 1H), 7.64 (m, 2H), 7.29 (m, 3H), 6.92 (t, 2H), 3.73 (t, 3H), 2.90 (t, 2H), 2.77 (t, 2H).

Example 4

Syntheses of Compounds 64-87 Listed in Table 1

Compounds 64-87 listed in Table 1 above were synthesized in a manner similar to that describe in Example 3. Their calculated mass and observed ESI-MS data are provided in Table 3.

TABLE 3

| Compd ID | Calculated Mass | Observed ESI-MS |
| --- | --- | --- |
| 64 | 346.08 | 344.8 (M − H)+ |
| 65 | 358.06 | 358.8 (M + H)+ |
| 66 | 341.07 | 341.8 (M + H)+ |
| 67 | 340.07 | 340.9 (M + H)+ |
| 68 | 370.08 | 370.8 (M + H)+ |
| 69 | 370.08 | 370.7 (M + H)+ |
| 70 | 371.08 | 372.0 (M + H)+ |
| 71 | 374.08 | 374.8 (M + H)+ |
| 72 | 344.07 | 345.0 (M + H)+ |
| 73 | 416.10 | 417.0 (M + H)+ |
| 74 | 358.10 | 358.5 (M + H)+ |
| 75 | 354.09 | 355.1 (M + H)+ |
| 76 | 422.18 | 423.0 (M + H)+ |
| 77 | 296.13 | 296.6 (M + H)+ |
| 78 | 345.15 | 345.7 (M + H)+ |
| 79 | 341.15 | 342.0 (M + H)+ |
| 80 | 338.11 | 338.6 (M + H)+ |
| 81 | 334.11 | 334.8 (M + H)+ |
| 82 | 335.11 | 335.8 (M + H)+ |
| 83 | 368.12 | 369.1 (M + H)+ |
| 84 | 364.12 | 365.0 (M + H)+ |
| 85 | 352.12 | 352.9 (M + H)+ |
| 86 | 348.13 | 349.0 (M + H)+ |
| 87 | 310.14 | 311.1 (M + H)+ |

Example 5

Hydrochloride salt of N-[5-(4-Methoxy-phenylsulfanyl)-thiazol-2-yl]-3-pyridin-3-yl-propionamide (70•HCl)

N-[5-(4-Methoxy-phenylsulfanyl)-thiazol-2-yl]-3-pyridin-3-yl-propionamide (70, 1.00 g) was dissolved in ethyl acetate, bubbled with HCl(g), and white solid was slowly generated. The precipitates were collected by filtration, washed with solvent and dried under vacuum to give hydrochloride salt of N-[5-(4-methoxy-phenylsulfanyl)-thiazol-2-yl]-3-pyridin-3-yl-propionamide (70.HCl): $^1H$ NMR (500

MHz, DMSO) δ8.87 (s, 1H), 8.80 (d, 1H), 8.51 (d, 1H), 8.01 (m, 1H), 7.67 (s, 1H), 7.27 (d, 2H), 6.92 (d, 2H), 3.73 (s, 3H), 3.12 (t, 2H), 2.90 (t, 2H).

Example 6

N-[5-(4-Methoxy-benzyl)-[1,3,4]thiadiazol-2-yl]-3-(5-methyl-furan-2-yl)-propionamide (88)

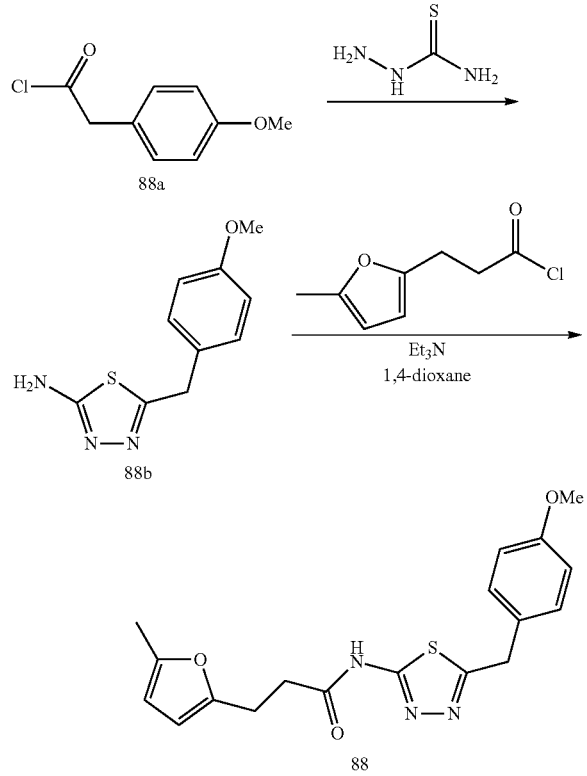

A mixture of 2-(4-methoxyphenyl)acetyl chloride (88a, 3.05 g, 16.5 mmol), and thiosemicarbazide (1.37 g, 15.0 mmol) were heated to 60° C. for 3.0 hours. The reaction mixture was then cooled to room temperature, quenched with water and extracted with ethyl acetate. The organic layer was washed with brine and 50% NaOH(aq), dried over. MgSO$_4$(s), and concentrated under reduced pressure to give 5-(4-methoxybenzyl)-1,3,4-thiadiazol-2-amine (88b).

To a solution of 5-(4-methoxybenzyl)-1,3,4-thiadiazol-2-amine (88b, 221 mg, 1.0 mmol), Et$_3$N (0.38 ml) in 1,4-dioxane (8.0 ml) was slowly added 3-(5-methylfuran-2-yl) propanoyl chloride and stirred for further 16.0 hours at room temperature. The reaction mixture was then quenched with water and extracted with ethyl acetate. The organic layer was washed with brine, dried over MgSO$_4$(s), and concentrated under reduced pressure to give N-[5-(4-methoxy-benzyl)-[1,3,4]thiadiazol-2-yl]-3-(5-methyl-furan-2-yl)-propionamide (88): $^1$H NMR (500 MHz, DMSO) δ7.24(d, 2H), δ6.89(d, 2H), δ5.90(d, 2H), δ4.24(s, 2H), δ3.72(s, 3H), δ2.83 (d, 3H), δ2.71(d, 2H), δ2.17(s, 3H). ESI-MS: 358.0 (M+H)$^+$.

Compounds 89 was synthesized in a manner similar to that describe above and its observed ESI-MS was 352.0 (M–H)$^+$.

Example 7

N-(1-Methyl-5-phenyl-1H-imidazol-2-yl)-3-phenyl-propionamide (90)

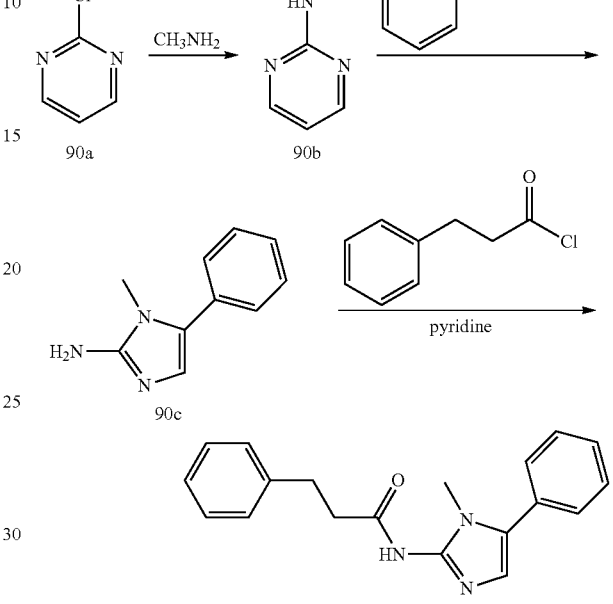

To a solution of 2-chloropyrimidine (90a, 2.0 g, 17.5 mmol) in THF (25 mL) was added 40% CH$_3$NH$_2$(aq) (7.5 mL) at 0° C. The reaction mixture was stirred at 50° C. for 1.0 hour and then poured into saturated NaHCO$_3$(aq) and extracted with ethyl acetate. The organic layer was washed with brine, dried over MgSO$_4$(s) and concentrated under reduced pressure to give N-methylpyrimidin-2-amine (90b).

To a microwave vial containing a solution of N-methylpyrimidin-2-amine (90b, 290 mg, 2.7 mmol) in acetonitrile (5 mL) was added 2-bromo-1-phenylethanone (714 mg, 3.6 mmol). The vial was sealed and heated in a microwave reactor at 130° C. for 20 minutes and then cooled to room temperature. The reaction mixture was treated with hydrazine hydrate (0.65 mL, 13.3 mmol) and then heated in a microwave reactor at 100° C. for 5.0 minutes. The solution was poured into water and filtered the precipitate to give 1-methyl-5-phenyl-1H-imidazol-2-ylamine (90c).

To a solution of 1-methyl-5-phenyl-1H-imidazol-2-amine (90c, 52.0 mg, 0.3 mmol) in pyridine (1.0 ml) was added 3-phenyl-propionyl chloride (60.7 mg, 0.36 mmol). The reaction mixture was stirred at room temperature for 16 hours, quenched with water and extracted with ethyl acetate. The organic layer was washed with brine, dried over MgSO$_4$(s) and concentrated under reduced pressure. The residue was purified by column chromatography on silica gel to give N-(1-Methyl-5-phenyl-1H-imidazol-2-yl)-3-phenyl-propionamide (90): $^1$H NMR (500 MHz, DMSO) δ: 7.16-7.48 (m, 10H), 6.87 (s, 1H), 3.42 (s, 3H), 3.07 (t, 2H), 2.92 (t, 2H). ESI-MS: 305.7 (M+H)$^+$.

Compounds 91 was synthesized in a manner similar to that describe above and its observed ESI-MS was 309.8 (M+H)$^+$.

Example 8

N-(5-(4-(Dimethylamino)phenyl)-3-methylpyridin-2-yl)-3-(5-methylfuran-2-yl) propanamide (120)

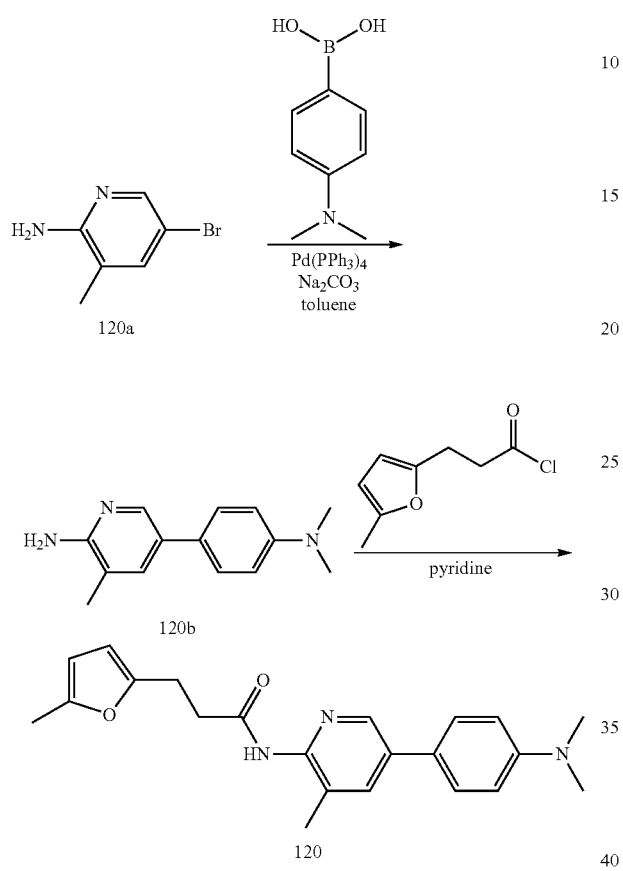

A solution of 5-bromo-3-methylpyridin-2-amine (120a, 1.87 g, 10.0 mmol) in toluene (60 mL) was treated with 4-(dimethylamino)phenylboronic acid (2.48 g, 15.0 mmol), Pd(PPh$_3$)$_4$ (345 mg, 0.30 mmol), and 2M Na$_2$CO$_3$(aq) (10 mL). The reaction mixture was heated to reflux for 18 hours and then cooled to room temperature. The reaction mixture was quenched with water and extracted with ethyl acetate. The organic layer was washed with brine, dried over MgSO$_4$(s) and concentrated under reduced pressure. The residue was purified by column chromatography on silica gel to give 5-(4-(dimethylamino)phenyl)-3-methylpyridin-2-amine (120b).

A solution of 5-(4-(dimethylamino)phenyl)-3-methylpyridin-2-amine (120b, 2.27 g, 10.0 mmol) in pyridine (30 ml) was added with 3-(5-methylfuran-2-yl)propanoyl chloride (1.90 g, 11.0 mmol) and then stirred at room temperature for further 16 hours. The reaction mixture was quenched with water and extracted with ethyl acetate. The organic layer was washed with brine, dried over MgSO$_4$(s) and concentrated under reduced pressure. The residue was purified by column chromatography on silica gel to give N-(5-(4-(Dimethylamino)phenyl)-3-methylpyridin-2-yl)-3-(5-methylfuran-2-yl) propanamide (120): $^1$H NMR (500 MHz, DMSO-d$^6$):δ: 9.99 (s, 1H), 8.46 (s, 1H), 7.84 (s, 1H), 7.55 (m, 2H), 6.81 (m, 2H), 5.98 (s, 1H), 5.94 (s, 1H), 2.94 (s, 6H), 2.87 (t, 2H), 2.65 (t, 2H), 2.21 (s, 3H), 2.16 (s, 3H).

Example 9

Syntheses of Compounds 92-122 Listed in Table 1

Compounds 92-122 listed in Table 1 above were synthesized in a manner similar to that describe in Example 8. Their calculated mass and observed ESI-MS data are provided in Table 4.

TABLE 4

| Compd ID | Calculated Mass | Observed ESI-MS |
|---|---|---|
| 92 | 307.13 | 307.9 (M + H)$^+$ |
| 93 | 301.12 | 301.8 (M + H)$^+$ |
| 94 | 303.14 | 325.7 (M + Na)$^+$ |
| 95 | 333.15 | 334.1 (M + H)$^+$ |
| 96 | 327.14 | 328.2 (M + H)$^+$ |
| 97 | 329.15 | 329.9 (M + H)$^+$ |
| 98 | 319.11 | 319.8 (M + H)$^+$ |
| 99 | 321.13 | 321.6 (M + H)$^+$ |
| 100 | 367.15 | 368.3 (M + H)$^+$ |
| 101 | 361.14 | 361.5 (M + H)$^+$ |
| 102 | 363.16 | 364.1 (M + H)$^+$ |
| 103 | 357.15 | 357.7 (M + H)$^+$ |
| 104 | 353.15 | 353.6 (M + H)$^+$ |
| 105 | 325.12 | 326.2 (M + H)$^+$ |
| 106 | 350.17 | 373.0 (M + Na)$^+$ |
| 107 | 367.15 | 389.9 (M + Na)$^+$ |
| 108 | 305.12 | 306.0 (M + H)$^+$ |
| 109 | 323.11 | 323.8 (M + H)$^+$ |
| 110 | 302.14 | 303.0 (M + H)$^+$ |
| 111 | 306.14 | 307.0 (M + H)$^+$ |
| 112 | 324.13 | 324.9 (M + H)$^+$ |
| 113 | 320.13 | 321.1 (M + H)$^+$ |
| 114 | 322.11 | 322.5 (M + H)$^+$ |
| 115 | 366.16 | 367.0 (M + H)$^+$ |
| 116 | 362.16 | 362.9 (M + H)$^+$ |
| 117 | 316.16 | 316.8 (M + H)$^+$ |
| 118 | 320.15 | 320.6 (M + H)$^+$ |
| 119 | 359.20 | 359.9 (M + H)$^+$ |
| 120 | 363.19 | 363.9 (M + H)$^+$ |
| 121 | 373.22 | 373.8 (M + H)$^+$ |
| 122 | 307.13 | 308.0 (M + H)$^+$ |

Example 10

Hydrochloride salt of N-(5-(4-(dimethylamino)phenyl)-3-methylpyridin-2-yl)-3-(5-methylfuran-2-yl) propanamide (120.HCl)

N-(5-(4-(Dimethylamino)phenyl)-3-methylpyridin-2-yl)-3-(5-methylfuran-2-yl) propanamide (120, 1.00 g) was dissolved in ethyl acetate, bubbled with HCl(g), and white solid was slowly generated. The precipitates were collected by filtration, washed with solvent and dried under vacuum to give hydrochloride salt of N-(5-(4-(dimethylamino)phenyl)-3-methylpyridin-2-yl)-3-(5-methylfuran-2-yl) propanamide: $^1$H NMR (500 MHz, DMSO-d$^6$): δ: 10.52 (br, 1H), 8.53 (s, 1H), 8.27 (s, 1H), 7.65 (m, 2H), 6.93 (br, 2H), 6.00 (s, 1H), 5.95 (s, 1H), 2.99 (s, 6H), 2.89 (t, 2H), 2.79 (t, 2H), 2.30 (s, 3H), 2.21 (s, 3H).

Example 11

N-(5-Bromo-pyridin-2-yl)-3-(5-methyl-furan-2-yl)-propionamide (123)

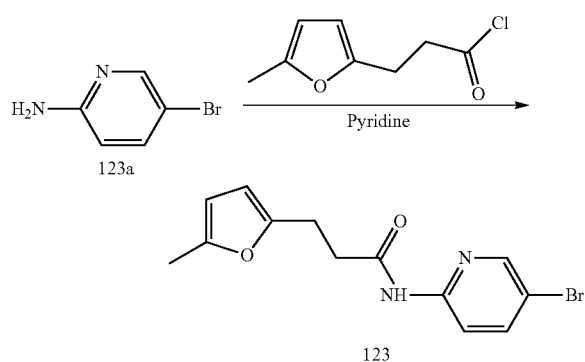

A solution of 5-bromopyridin-2-amine (123a, 600 mg, 3.47 mmol) in pyridine (10 ml) was added 3-(5-Methyl-furan-2-yl)-propionyl chloride (718.3 mg, 4.16 mmol) and stirred at room temperature for 16 hours. The reaction mixture was then quenched with water and extracted with ethyl acetate. The organic layer was washed with brine, dried over $MgSO_4$(s) and concentrated under reduced pressure. The residue was purified by column chromatography on silica gel to give N-(5-Bromo-pyridin-2-yl)-3-(5-methyl-furan-2-yl)-propionamide (123): $^1$H NMR (500 MHz, DMSO) δ: 10.68 (s, 1H), 10.68 (s, 1H), 8.42 (d, 1H), 8.07 (m, 1H), 5.94 (s, 1H), 5.92 (s, 1H), 2.85 (t, 2H), 2.70 (t, 2H), 2.19 (s, 3H). ESI-MS: 310.2 $(M+H)^+$.

Compounds 124 was synthesized in a manner similar to that describe above and its observed ESI-MS was 325.1 $(M+H)^+$.

Example 12

MTS assay

MTS assay was performed in determining the growth inhibition of cancer cells. MTS ((3-(4,5-dimethylthiazol-2-yl)-5-(3-carboxymethoxyphenyl)-2-(4-sulfophenyl)-2H-tetrazolium)), in the presence of phenazine methosulfate (PMS) and reductases, produces a formazan product that has an absorbance maximum at 490-500 nm. MTS assays (and closely related MTT assay) are commonly used to measure cell viabilities or survivals.

Briefly, KB/Hela, NCI-H460, A375, Colo205, HCT-116, U937, MCF-7, MDA-MB-231, A549, H1975 cells were seeded into 96-well plate at 4000, 4000, 2000, 2000, 2000 cells/well. After 24 h for attachment, test compound was added into each well and incubated for 72 h. A total of 20 μl of MTS reaction reagent containing the MTS (Promega, Madison, Wis.) and PMS in a ratio of 20:1 was added into each well to react with dehydrogenase enzyme in survival cells. After 3 h, the absorbance at 490 nm was monitored using Emax precision microplate reader (Molecular Devices, Sunnyvale, Calif.).

The growth inhibition rate of MTS assay at KB cell of these compounds (at 10 μM concentration) are list in Table 5.

TABLE 5

| Entry | Inhibition rate (%) |
|---|---|
| 1 | 95.4 |
| 2 | 95.5 |
| 3 | 94.3 |
| 4 | 93.9 |
| 5 | 95.8 |
| 6 | 95.1 |
| 7 | 91.7 |
| 8 | 90.6 |
| 9 | 96.1 |
| 10 | 94.4 |
| 11 | 95.1 |
| 12 | 96.0 |
| 13 | 94.6 |
| 14 | 89.5 |
| 15 | 93.0 |
| 16 | 62.0 |
| 17 | 95.9 |
| 18 | 96.6 |
| 19 | 94.1 |
| 20 | 93.4 |
| 21 | 97.1 |
| 22 | 95.6 |
| 23 | 95.8 |
| 24 | 95.2 |
| 25 | 94.2 |
| 26 | 92.9 |
| 27 | 91.2 |
| 28 | 95.0 |
| 29 | 96.6 |
| 30 | 92.3 |
| 31 | 95.8 |
| 32 | 52.7 |
| 33 | 92.4 |
| 34 | 92.8 |
| 35 | 90.4 |
| 36 | 94.3 |
| 37 | 94.4 |
| 38 | 94.2 |
| 39 | 94.0 |
| 40 | 58.8 |
| 41 | 95.8 |
| 42 | 91.2 |
| 43 | 95.6 |
| 44 | 93.1 |
| 45 | 94.0 |
| 46 | 96.0 |
| 47 | 94.5 |
| 48 | 95.3 |
| 49 | 95.1 |
| 50 | 97.2 |
| 51 | 96.1 |
| 52 | 94.5 |
| 53 | 96.7 |
| 54 | 96.1 |
| 55 | 95.1 |
| 56 | 94.7 |
| 57 | 93.2 |
| 58 | 85.8 |
| 59 | 93.5 |
| 60 | 95.1 |
| 61 | 90.9 |
| 62 | 96.0 |
| 63 | 95.6 |
| 64 | 95.9 |
| 65 | 96.3 |
| 66 | 93.3 |
| 67 | 96.6 |
| 68 | 94.4 |
| 69 | 87.6 |
| 70 | 78.5 |
| 71 | 94.4 |
| 72 | 60.0 |
| 73 | 97.0 |
| 74 | 96.9 |

TABLE 5-continued

| Entry | Inhibition rate (%) |
|---|---|
| 75 | 82.5 |
| 76 | 95.0 |
| 77 | 87.3 |
| 78 | 93.9 |
| 79 | 73.7 |
| 80 | 79.4 |
| 81 | 95.1 |
| 82 | 95.6 |
| 83 | 95.2 |
| 84 | 94.7 |
| 85 | 76.8 |
| 86 | 92.8 |
| 87 | 93.9 |
| 88 | 93.5 |
| 89 | 96.9 |
| 90 | 96.6 |
| 91 | 96.0 |
| 92 | 97.1 |
| 93 | 96.0 |
| 94 | 97.4 |
| 95 | 93.6 |
| 96 | 96.8 |
| 97 | 52.7 |
| 98 | 81.9 |
| 99 | 95.8 |
| 100 | 97.8 |
| 101 | 97.5 |
| 102 | 94.5 |
| 103 | 94.1 |
| 104 | 96.6 |
| 105 | 96.7 |
| 106 | 84.6 |
| 107 | 97.0 |
| 108 | 96.9 |
| 109 | 95.9 |
| 110 | 97.0 |
| 111 | 65.1 |
| 112 | 96.2 |
| 113 | 97.1 |
| 114 | 93.4 |
| 115 | 95.8 |
| 116 | 94.1 |
| 117 | 94.6 |
| 118 | 93.0 |
| 119 | 95.1 |
| 120 | 85.9 |
| 121 | 93.5 |
| 122 | 80.8 |
| 123 | 95.8 |
| 124 | 93.3 |

The $IC_{50}$ values from MTS assays for 70 on other cancer cell lines are as follows: Colo205, 68.2 nM; U937, 23.2 nM; A375, 34.6; MDA-MB-231, 182 nM; A549, 58 nM; H1975, 141 nM.

Example 13

Tubulin Polymerization Assay

In vitro tubulin polymerization assay was performed by using the Tubulin Polymerization Assay Kit (Cytoskeleton, Inc., Denver, Colo.) in a 96-well format, which used the polymerization of porcine brain tubulin in vitro in the presence of varying concentrations of the test compounds. Fluorescence measurements were obtained at 1-minute intervals over a 31-minute period. Fluorescent measurements were performed using excitation at 365 nm, and emission was measured at 440 nm using a Packard Fusion Alpha Microplate Analyzer. Data were analyzed as relative fluorescent units by GraphPad Prism 5 Demo.

The inhibition rate of tubulin polymerization assay (at 10 µM concentration) are listed in Table 6.

TABLE 6

| Entry | Inhibition rate (%) |
|---|---|
| 9 | 79.0 |
| 10 | 88.7 |
| 17 | 65.3 |
| 47 | 57.2 |
| 52 | 51.2 |
| 53 | 62.2 |
| 55 | 54.9 |
| 58 | 55.1 |
| 69 | 50.5 |
| 70 | 59.6 |
| 71 | 60.1 |
| 77 | 60.8 |
| 79 | 53.2 |
| 83 | 64.7 |
| 84 | 50.3 |
| 85 | 54.0 |
| 92 | 74.0 |
| 94 | 55.2 |
| 99 | 55.8 |
| 100 | 84.3 |
| 102 | 58.6 |
| 105 | 72.2 |
| 106 | 69.3 |
| 111 | 72.7 |
| 112 | 76.9 |
| 118 | 81.4 |
| 120 | 51.8 |
| 123 | 85.6 |
| 124 | 84.9 |

Example 14

Colchicine Competitive-binding Assay

The colchicine competitive-binding assay was done by using the Colchicine Site competitive Assay Kit (Cytoskeleton, Inc.), streptavidin-coated yttrium SPA beads(GE Healthcare, Inc.), and $^3$H-colchicine(PerkinElmer, Inc.). Briefly, the binding mixture includes 1 µL $^3$H-labeled ligand (specific activity 20-80 Ci/µL), and 1 µg biotinylated tubulin and 88 µg SPA beads in 200 µL assay buffer. The test compound and $^3$H-labeled ligand were added before tubulin. After incubation at 37° C. for 2 hours, the SPA beads were allowed to settle down for 24 hours at room temperature, and scintillation counting was done on the TopCount Microplate Scintillation Counter.

The rate of colchicine competitive-binding (at 10 µM concentration) are listed in Table 7.

TABLE 7

| Entry | binding rate (%) | Entry | Inhibition rate (%) |
|---|---|---|---|
| 1 | 50.2 | 77 | 99.8 |
| 4 | 58.6 | 79 | 90.0 |
| 5 | 63.8 | 81 | 70.0 |
| 6 | 63.6 | 83 | 91.9 |
| 9 | 77.5 | 84 | 88.0 |
| 10 | 88.6 | 85 | 92.6 |
| 11 | 62.4 | 87 | 54.6 |
| 12 | 51.2 | 92 | 94.7 |
| 13 | 60.0 | 93 | 57.2 |
| 17 | 76.9 | 94 | 82.9 |
| 47 | 55.4 | 98 | 57.5 |
| 49 | 64.9 | 99 | 78.3 |
| 52 | 75.4 | 100 | 83.4 |
| 53 | 78.7 | 101 | 56.9 |
| 54 | 73.3 | 102 | 59.2 |
| 55 | 68.8 | 103 | 81.1 |
| 56 | 88.3 | 104 | 61.3 |
| 59 | 76.3 | 105 | 99.3 |

TABLE 7-continued

| Entry | binding rate (%) | Entry | Inhibition rate (%) |
|---|---|---|---|
| 60 | 64.6 | 106 | 70.1 |
| 61 | 57.9 | 111 | 96.4 |
| 62 | 55.3 | 112 | 87.8 |
| 63 | 63.3 | 118 | 99.7 |
| 64 | 54.4 | 119 | 58.2 |
| 69 | 85.2 | 120 | 97.5 |
| 70 | 92.9 | 123 | 78.4 |
| 71 | 86.0 | 124 | 74.8 |

Example 15

Capillary Disruption Assays

Capillary disruption assays were carried out in μ-Slide Angiogenesis using HUVEC cells plated at 20,000 cells per well in EGM-2 medium on a Matrigel layer (BD Biosciences). Capillaries were allowed to form over a 16 hours period before the addition of compound 70 or control. Cells were stained using calcein AM (Calbiochem) at room temperature for 40 minutes after a brief washing step. Images were acquired immediately following compound addition and 6 hours after exposure to test compound. Capillary disruption assay results were analyzed with Automated Image Analysis on Wimasis Image Analysis Platform. The results of capillary disruption assays are shown in FIG. 1.

Example 16

Capillary Formation Assays

Figure 2:
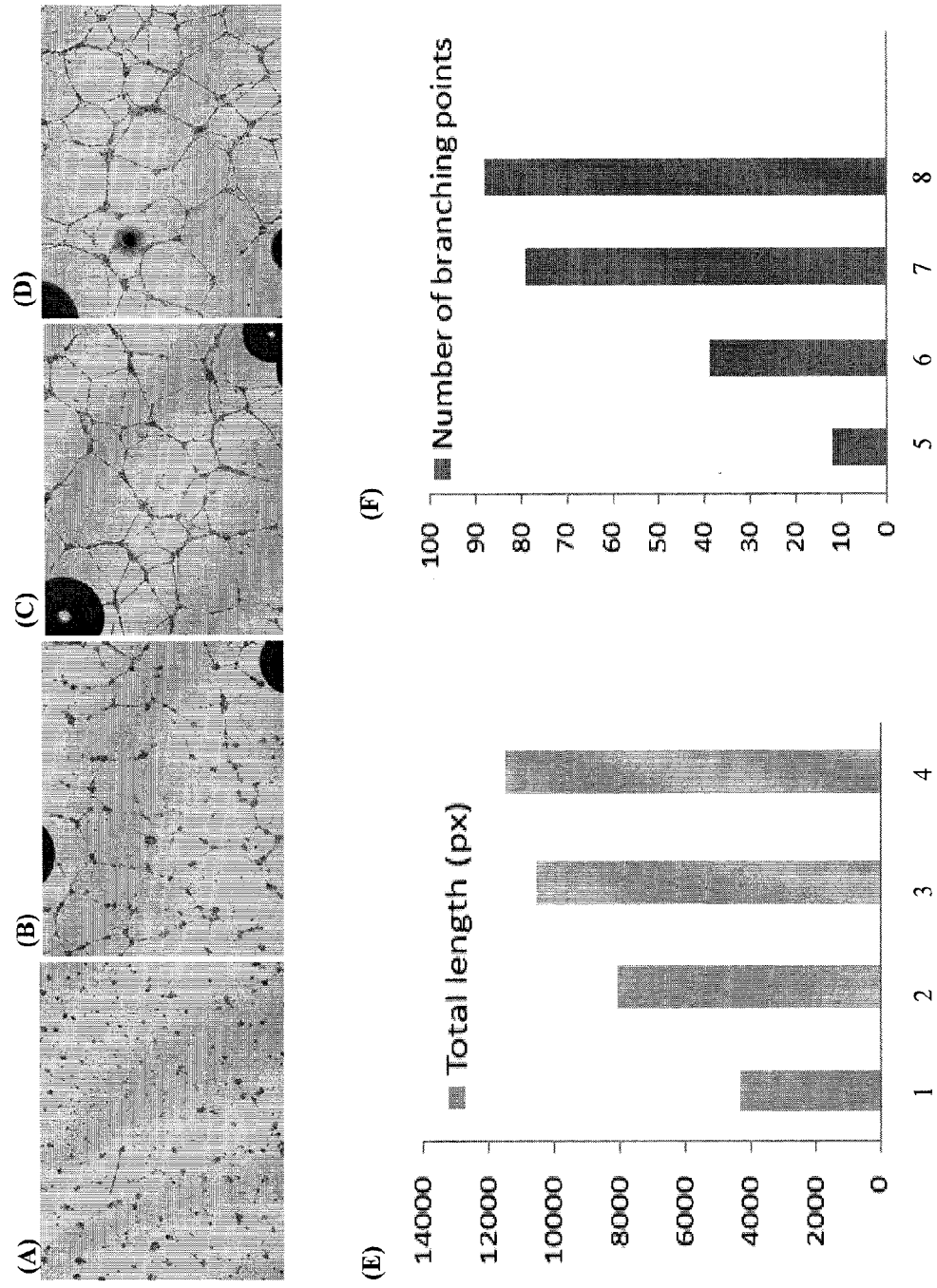
FIGS. 2(A)-2(F) show results of capillary formation assays in accordance with embodiments of the invention. The images of HUVEC cells treated with compound 70 at 100 nM (A), 30 nM (B), 10 nM (C), and 0 nM (D) for 6.0 hours. (E) Capillary total length of HUVEC cells. Lane 1, 2, 3, 4 were measured after treatment with 70 at 100 nM, 30 nM, 10 nM, and 0 nM for 6.0 hours, respectively. (F) Number of capillary branching points of HUVEC cells. Lane 5, 6, 7, 8 were measured after treatment with compound 70 at 100 nM, 30 nM, 10 nM, and 0 nM for 6.0 hours, respectively.

Capillary formation assays were conducted in μ-Slide Angiogenesis (ibidi GmbH) using HUVEC cells plated on a Matrigel layer (BD Biosciences) with 20,000 cells per well, respectively, and incubated for 22 hours. Capillaries were allowed to form over a 16 hour period before the addition of compound 70 or control. Cells were stained using calcein AM (Calbiochem) at room temperature for 40 minutes after a brief washing step. Images were acquired immediately following compound addition and 6 hours after exposure to the test compound. Capillary formation assay results were analyzed with Automated Image Analysis on Wimasis Image Analysis Platform. The results of capillary formation assays are shown in FIG. 2.

Example 17

Cell Cycle Analysis by Flow Cytometry (FACS)

Figure 3:
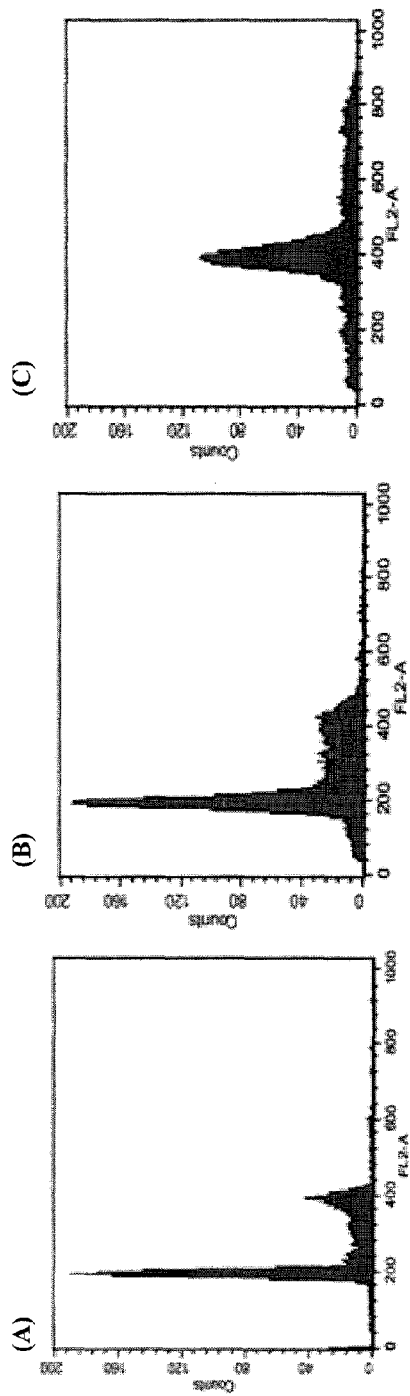
FIGS. 3(A)-3(C) show results of cell cycle analysis by flow cytometry (FACS) in accordance with one embodiment of the invention. Cell cycle profiles of A375 cells treated with various concentrations of compound 70 for 24 h. (A), 0 nM; (B), 100 nM; (C), 300 nM.

Compound 70 treated A375 cells were harvested by trypsinization, washed in PBS, resuspended in ice-cold 70% ethanol and store at −20° C. overnight. Cells were then washed twice with PBS and resuspended in PBS containing 2 μg/mL RNase A and 5 μg/mL propidium iodide and stained for 30 min. DNA content was analyzed by FACSan (Becton Dickinson) using CellQuest software. The results of cell cycle analysis by flow cytometry were shown in FIG. 3.

Example 18

In vivo Pharmacokinetics Studies

Figure 4:
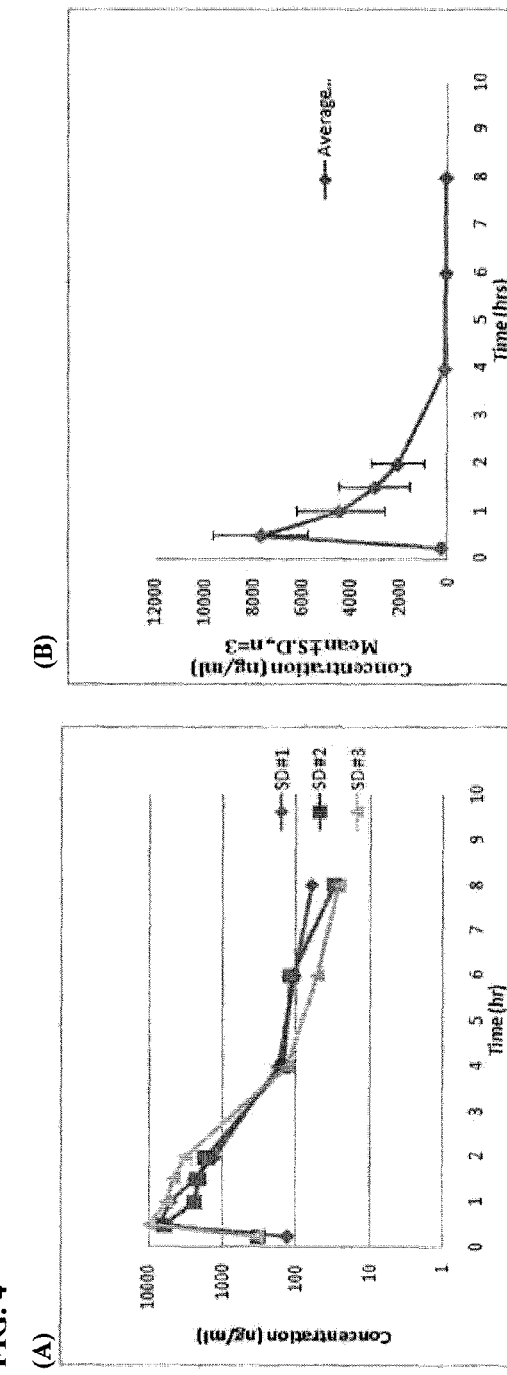
FIGS. 4(A)-4(B) show results of in vivo pharmacokinetics in accordance with one embodiment of the invention. Plasma concentration of Sprague-Dawley rats treated with compound 70 via different administration. (A), oral gavage; (B), bolus intravenous.

For in vivo pharmacokinetics studies, fasted male Sprague-Dawley rats were given compound 70 for 20 mg/kg by oral gavage and 2 mg/kg by bolus intravenous injection and the number of rats for each administering route is 3. The plasma samples will be collected at eight time-points: 0, 5, 15, 30, 60, 120, 240, 360 and 480 minutes. Oral bioavailability was determined using a solution of the 10% NMP, 50% PEG-200 in water. All biological samples from the blood will be collected and analyzed by a validated LC-MS/MS system. Data of plasma concentration and pharmacokinetic parameters of each individual animal and the "Mean±SD" of each group are reported. Non-compartmental pharmacokinetic parameters, including systemic clearance (CL), volume of distribution at steady state (Vss), elimination half-life ($t_{1/2}$) and mean residence time (MRT), the area under the concentration-time curve from time 0 extrapolated to infinity ($AUC_{(0-\infty)}$), and area under the concentration-time curve from time 0 to the last measurable concentration ($AUC_{(0-t)}$), of each rat is calculated using WinNolin program. The results of in vivo pharmacokinetics studies were shown in FIG. 4.

Example 19

In vivo Xenograft Tumor Efficacy Studies

Figure 5:
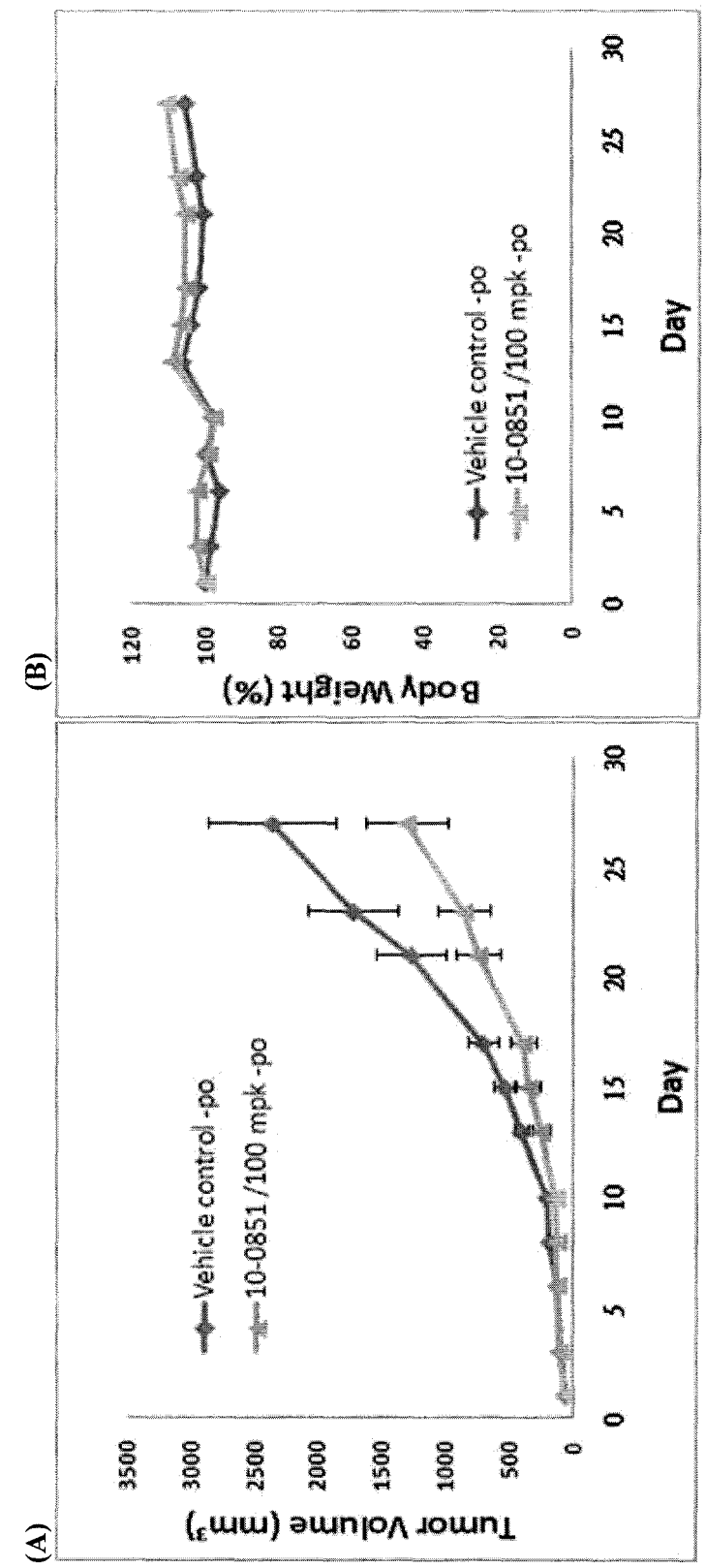
FIGS. 5(A)-5(B) show results of In vivo tumor growth and body weight determination of compound 70 in A375 melanoma xenograft in accordance with one embodiment of the invention.

A375($1 \times 10^6$ cell/mouse) tumor cells were subcutaneously injected into the right flank of 5 week old male NOD/SCID mice (BioLASCO, Taiwan). Tumor volume was measured with a digital caliper once tumor was palpable (within 10 to 15 days after implantation). The tumor-bearing animals were treated when the size of tumor have reached to an average volume of ~100 to 150 mm³. All the mice were divided into 2 groups and treated orally with compound 70 (100 mg/kg) or vehicle control (10% NMP, 50% PEG-200 in H2O) twice daily for 21 days. The test compound 70 was formulated in a solution of 10% NMP, 50% PEG-200 and 40% H2O. Body weights of the mice were measured every two days and the size of tumor was measured by a digital caliper every two days. The tumor size plotted in FIG. 5 represents the mean+/−S.E. of data from 5 mice.

Example 20

In vivo Orthotropic Xenograft Tumor Efficacy Studies

Figure 6:
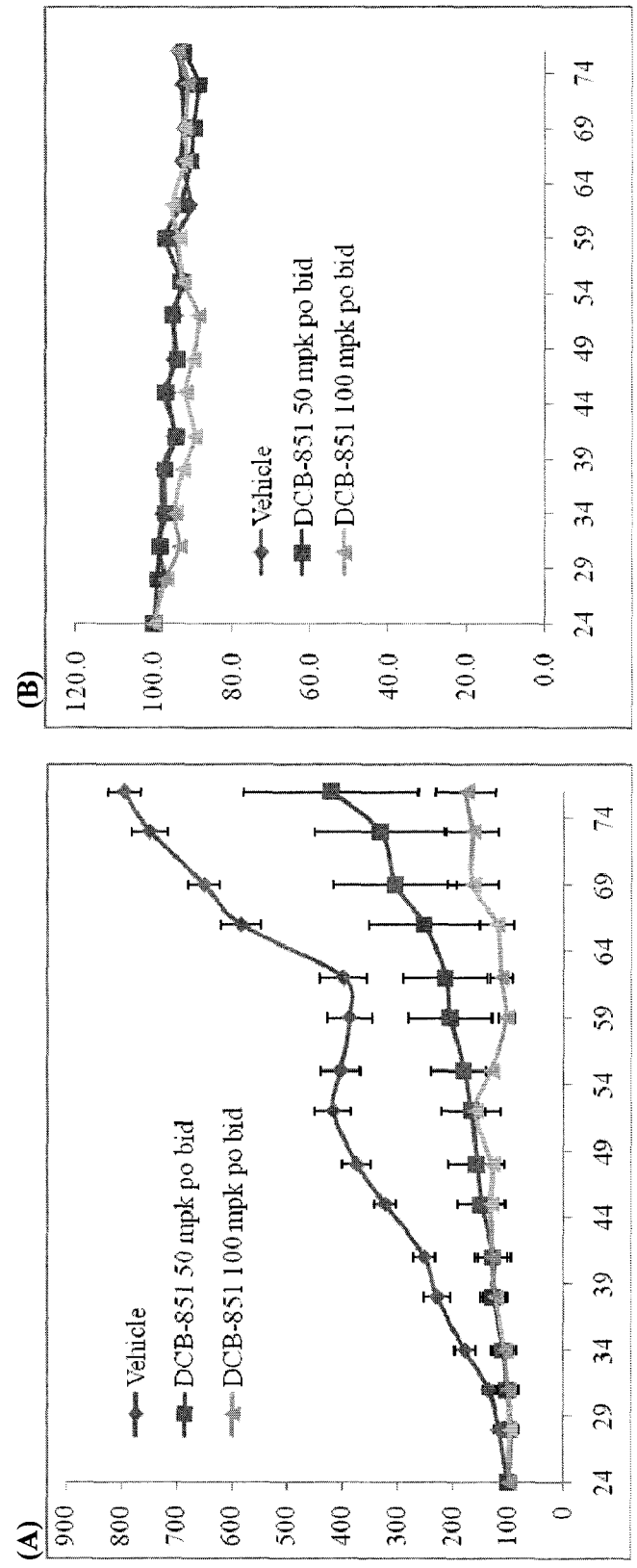
FIGS. 6(A)-6(B) show results of In vivo tumor growth inhibition and body weight determination of compound 70 for MCF-7 breast cancer orthotropic xenograft in accordance with one embodiment of the invention.

MCF-7($1 \times 10^7$ cell/mouse) human breast cancer cells were subcutaneously injected into the mammary fat pad of 8 weeks old nu/nu nude mice (BioLASCO, Taiwan) and resuspended in 100 μL of a 50% Matrigel solution (BD Biosciences, MA, USA) for 7 days after their implantation with a 17-β-estradiol pellet (0.72 mg; 60-day release, Innovative Research of America, FL, USA). Tumor volume was measured with a digital caliper once tumor was palpable (within 10 to 15 days after implantation). The tumor-bearing animals were treated when the size of tumor have reached to an average volume of ~100 mm³. The mice were then sorted and randomly divided into three groups of 6 mice each and treated with various concentrations of compound 70 (100 mg/kg and 50 mg/kg) or vehicle (5% DMSO, 10% cremophor EL in H2O) by gavage twice a day for 28 consecutive days. The test compound 70 were formulated in a solution of 5% DMSO, 10% cremophor EL and 85% H2O. Body weights of the mice were measured twice a week and the size of tumor was measured by a digital caliper twice a week. The tumor size plotted in FIG. 6 represents the mean+/−S.E. of data from 5 mice.

Example 21

Pathological Evaluation

Figure 7:
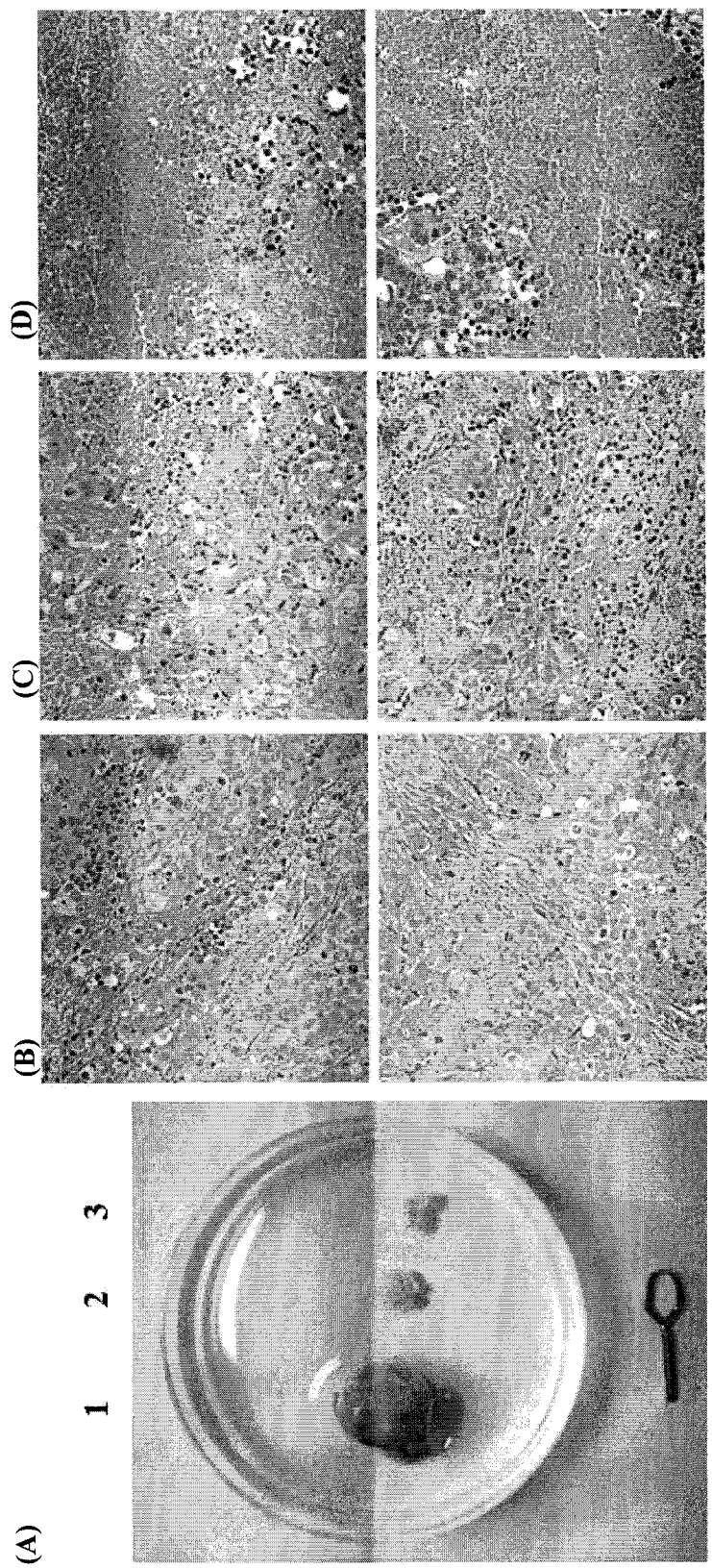
FIGS. 7(A)-7(D) show images of tumor and histopathology in accordance with one embodiment of the invention. (A), Tumors of rats treated with various concentration of compound 70. Lane 1, Control; Lane 2, 50 mg/kg; Lane 3, 100 mg/kg. (B)-(D), histopathology of tumors of rats treated with various concentration of compound 70. (B), Control; (C), 50 mg/kg; (D), 100 mg/kg.
Figure 8:
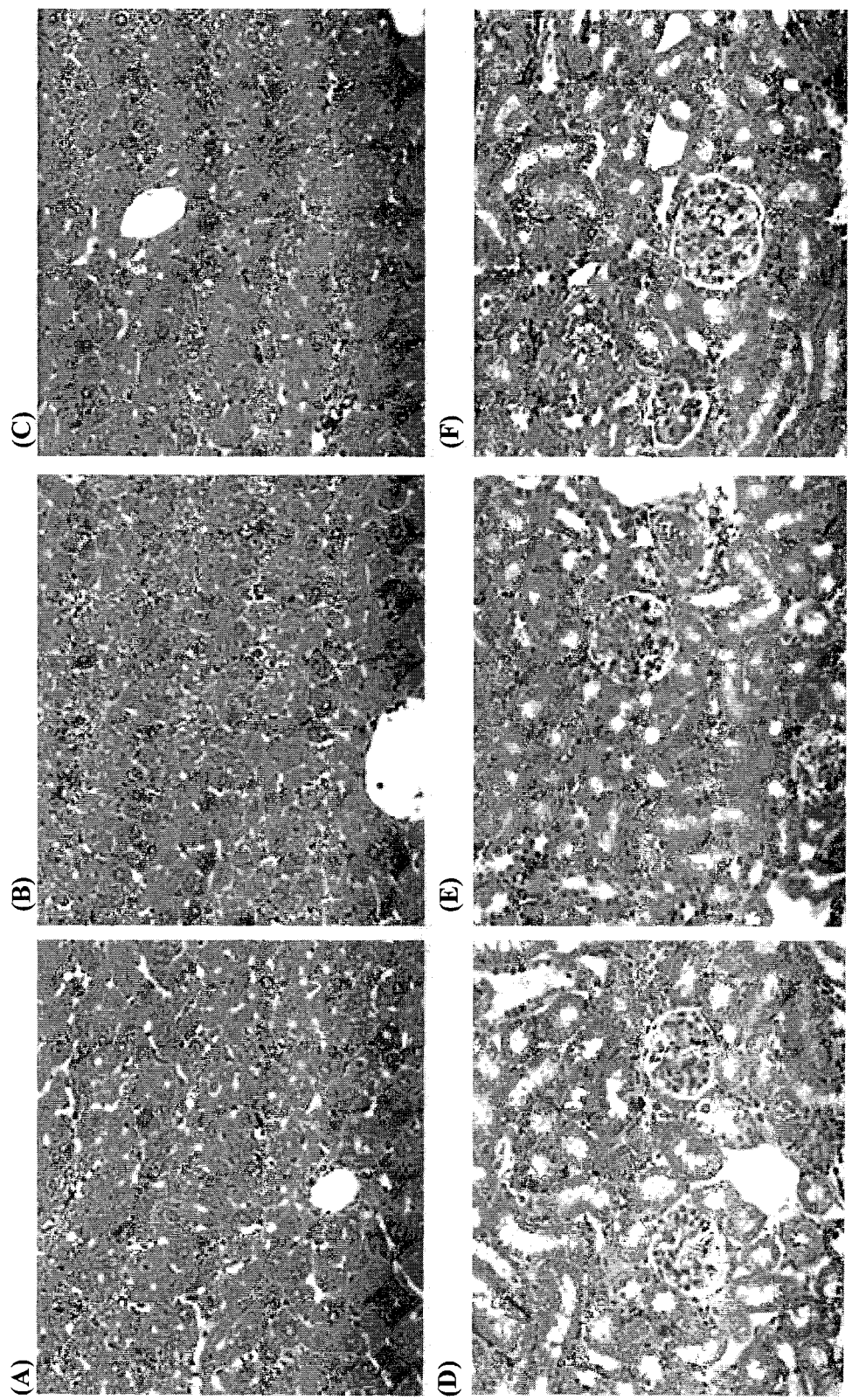
FIGS. 8(A)-8(F) show results of histopathology of different organs in rats treated with various concentration of compound 70 in accordance with one embodiment of the invention. (A), liver, control; (B), liver, 70, 50 mg/kg; (C), liver, 70, 100 mg/kg; (D), kidney, control; (E), kidney, 70, 50 mg/Kg; (F), kidney, 70, 100 mg/Kg.

For histopathology, the tissues were fixed in 10% buffered formalin and embedded in paraffin, and then sections (4 μm)

were prepared and stained with hematoxylin and eosin. The pathology of liver, kidney, and tumor were determined in a blinded fashion by a pathologist. The results of pathological evaluation of in vivo orthotropic MCF-7 xenograft studies were shown in FIGS. 7 and 8.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A compound for inhibition of tubulin polymerization having a structure shown in formula (Ib) or a pharmaceutically acceptable salt thereof,

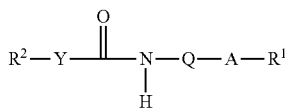

Ib wherein A is $CH_2$, O, S, or NH; Q is thiazole; Y is $CH_2$—$CH_2$; $R^1$ and $R^2$ are each independently selected from the group consisting of aryl, and heteroaryl, provided that the heteroaryl does not include furan or thiophene, wherein said aryl and heteroaryl are each optionally substituted with one or more substituents selected from $R^f$ and $R^g$, wherein $R^f$ and $R^g$ are each independently selected from the group consisting of: hydrogen, halogen, $(C_{1-4})$alkyl, $(C_{1-4})$alkoxyl, O—$(C_{1-4})$alkyl, S—$(C_{1-4})$ alkyl, aryl, heteroaryl, $N(R^c)(R^d)$, $COR^c$, $CON(R^c)(R^d)$, $NR^c$—CO—$N(R^c)(R^d)$, O—CO—$N(R^c)$ $(R^d)$, $NR^c$—$S(O)_n$—$N(R^c)(R^d)$, or $R^f$ and $R^g$ can join together with carbon, nitrogen or sulfur atoms to which they are attached to form a ring selected from the group consisting of a cycloalkyl and a heterocycloalkyl, $R^c$ and $R^d$ are each independently selected from the group consisting of hydrogen, halogen, $(C_{1-6})$alkyl, $(C_{1-6})$alkoxyl, $(C_{6-19})$aryl, heteroaryl, $(C_{3-12})$cycloalkyl, or $R^c$ and $R^d$ can join together with carbon, nitrogen or sulfur atoms, to which they are attached, to form a 5-7 membered ring; and n is 0, 1, or 2.

2. The compound according to claim 1,
wherein $R^1$ and $R^2$ are each independently selected from the group consisting of phenyl, pyrrole, thiazole, imidazole, oxadiazole, tiadiazole, pyridine, pyrimidine, pyridazine, pyrazine, indole and naphthalene, wherein each group is optionally substituted with one or more substituents selected from $R^f$ and $R^g$, wherein $R^f$ and $R^g$ are each independently selected from the group consisting of: hydrogen, halogen, $(C_{1-4})alkyl$, $(C_{1-4})$alkoxyl, O—$(C_{1-4})$alkyl, S—$(C_{1-4})$alkyl, aryl, heteroaryl, $N(R^c)$ $(R^d)$, $COR^c$, $CON(R^c)(R^d)$, $NR^c$—CO—$N(R^c)(R^d)$, O—CO—$N(R^c)(R^d)$, $NR^c$—$S(O)_n$—$N(R^c)(R^d)$, or $R^f$ and $R^g$ can join together with carbon, nitrogen or sulfur atoms, to which they are attached, to form a ring selected from the group consisting of a cycloalkyl and a heterocycloalkyl.

3. The compound according to claim 1,
wherein $R^1$ and $R^2$ are each independently selected from the group consisting of phenyl, thiazole, pyridine, pyrimidine, indole and naphthalene, wherein each group is optionally substituted with one or more substituents selected from $R^f$ and $R^g$, wherein $R^f$ and $R^g$ are each independently selected from the group consisting of: hydrogen, halogen, $(C_{1-4})$alkyl, $(C_{1-4})$alkoxyl, O—$(C_{1-4})$alkyl, S—$(C_{1-4})$alkyl, aryl, heteroaryl, $N(R^c)(R^d)$, $COR^c$, $CON(R^c)(R^d)$, $NR^c$—CO—$N(R^c)(R^d)$, O—CO—$N(R^c)(R^d)$, $NR^c$—$S(O)_n$—$N(R^c)(R^d)$, or $R^f$ and $R^g$ can join together with carbon, nitrogen or sulfur atoms, to which they are attached, to form a ring selected from the group consisting of a cycloalkyl and a heterocycloalkyl.

4. The compound according to claim 1,
wherein; $R^1$ and $R^2$ are each independently selected from the group consisting of phenyl, pyridine, pyrimidine, and naphthalene, wherein each group is optionally substituted with one or more substituents selected from $R^f$ and $R^g$, wherein $R^f$ and $R^g$ are each independently selected from the group consisting of: hydrogen, halogen, $(C_{1-4})$alkyl, $(C_{1-4})$alkoxyl, O—$(C_{1-4})$alkyl, S—$(C_{1-4})$ alkyl, aryl, heteroaryl, $N(R^c)(R^d)$, $COR^c$, $CON(R^c),(R^d)$, $NR^c$—CO—$N(R^c)(R^d)$, O—CO—N $(R^c)(R^d)$, $NR^c$—$S(O)_n$—$N(R^c)(R^d)$, or $R^f$ and $R^g$ can join together with carbon, nitrogen or sulfur atoms, to which they are attached, to form a ring selected from the group consisting of a cycloalkyl and a heterocycloalkyl.

5. The compound according to claim 1,
wherein $R^1$ and $R^2$ are each independently selected from the group consisting of phenyl and pyridine, wherein each group is optionally substituted with one or more substituents selected from $R^f$ and $R^g$, wherein $R^f$ and $R^g$ are each independently selected from the group consisting of: hydrogen, halogen, $(C_{1-4})$alkyl, $(C_{1-4})$alkoxyl, O—$(C_{1-4})$alkyl, S—$(C_{1-4})$ alkyl, aryl, heteroaryl, $N(R^c)$ $(R^d)$, or $R^f$ and $R^g$ can join together with carbon, nitrogen or sulfur atoms, to which they are attached, to form a ring selected from the group consisting of a cycloalkyl and a heterocycloalkyl.

6. The compound according to claim 1, wherein the compound is:
N-(5-Benzyl-thiazol-2-yl)-3-phenyl-propionamide;
N-[5-(4-Fluoro-benzyl)-thiazol-2-yl]-3-pyridin-3-yl-propionamide;
N-(5-Benzo[1,3]dioxol-5-ylmethyl-thiazol-2-yl)-3-phenyl-propionarnide;
N-(5-Benzo[1,3]dioxol-5-ylmethyl-thiazol-2-yl)-3-(4-fluoro-phenyl)-propionamide;
N-(5-Benzo[1,3]dioxol-5-ylmethyl-thiazol-2-yl)-3-pyridin-3-yl-propionamide;
N-[5-(4-Methoxy-benzyl)-thiazol-2-yl]-3-phenyl-propionamide;
N-[5-(4-Methoxy-benzyl)-thiazol-2-yl]-3-pyridin-3-yl-propionamide;
3-(4-Fluoro-phenyl)-N-[5-(4-methoxy-benzyl)-thiazol-2-yl]-propionamide;
N-[5-(4-Fluoro-benzyl)-thiazol-2-yl]-3-(4-fluoro-phenyl)-propionamide;
3-(4-Fluoro-phenyl)-N-[5-(6-methoxy-naphthalen-2-yl-methyl)-thiazol-2-yl]-propionamide;
N-[5-(6-Methoxy-naphthalen-2-ylmethyl)-thiazol-2-yl]-3-phenyl-propionamide;
N-[5-(4-Methoxy-benzyl)-thiazol-2-yl]-3-(4-methoxy-phenyl)-propionamide;
N-[5-(4-Methoxy-benzyl)-thiazol-2-yl]-3-pyridin-4-yl-propionamide;
N-[5-(3,4-Dimethoxy-benzyl)-thiazol-2-yl]-3-pyridin-3-yl-propionamide;
N-[5-(3,4-Dimethoxy-benzyl)-thiazol-2-yl]-3-(4-fluoro-phenyl)-propionamide;

N-[5-(3,4-Dimethoxy-benzyl)-thiazol-2-yl]-3-(4-methoxy-phenyl)-propionamide;
N-(5-Naphthalen-2-ylmethyl-thiazol-2-yl)-3-phenyl-propionamide;
3-(4-Fluoro-phenyl)-N-(5-naphthalen-2-ylmethyl-thiazol-2-yl)-propionamide;
N-(5-Naphthalen-2-ylmethyl-thiazol-2-yl)-3-pyridin-3-yl-propionamide;
N-[5-(3,4-Difluoro-benzyl)-thiazol-2-yl]-3-phenyl-propionamide;
N-[5-(3,4-Difluoro-benzyl)-thiazol-2-yl]-3-(3-methoxy-phenyl)-propionamide;
N-[5-(3,4-Difluoro-benzyl)-thiazol-2-yl]-3-pyridin-3-yl-propionarnide;
N-[5-(3,4-Difluoro-benzyl)-thiazol-2-yl]-3-(4-fluoro-phenyl)-propionamide;
N-[5-(3,4-Dimethoxy-benzy)-thiazol-2-yl]-3-(3-methoxy-phenyl)-propionamide;
N-(5-Pentafluorophenylmethyl-thiazol-2-yl)-3-phenyl-propionamide;
3-(3-Methoxy-phenyl)-N-(5-pentafluorophenylmethyl-thiazol-2-yl)-propionamide;
N-(5-Pentafluorophenylmethyl-thiazol-2-yl)-3-pyridin-3-yl-propionamide;
3-(3-Fluoro-phenye-N-(5-naphthalen-2-ylmethyl-thiazol-2-yl)-propionamide;
3-(3-Methoxy-phenyl)-N-(5-naphthalen-2-ylmethyl-thiazol-2-yl)-propionanaide;
N-(5-Biphenyl-4-ylmethyl-thiazol-2-yl)-3-(4-fluoro-phenyl)-propionamide;
N-(5-Biphenyl-4-ylmethyl-thiazol-2-yl)-3-pyridin-3-yl-propionamide;
3-(4-Fluoro-phenyl)-N-[5-(4-trifluoromethyl-benzyl)-thiazol-2-yl]-propionamide;
3-Pyridin-3-yl-N[5-(4-trifluoromethyl-benzyl)-thiazol-2-yl]-propionamide;
3-Phenyl-N-[5-(4-trifluoromethyl-benzyl)-thiazol-2-yl]-propionamide;
3-(3-Methoxy-phenyl)-N-[5-(4-trifluoromethyl-benzyl)-thiazol-2-yl]-propionamide;
3-Phenyl-N-[5-(3,4,5-trimethoxy-benzyl)-thiazol-2-yl]-propionamide;
3-Pyridin-3-yl-N-[5-(3,4,5-trimethoxy-benzyl)-thiazol-2-yl]-propionamide;
3-Biphenyl-4-yl-N-[5-(4-methoxy-benzyl)-thiazol-2-yl]-propionamide;
3-Phenyl-N-[5-(2,3,4-trimethoxy-benzyl)-thiazol-2-yl]-propionamide;
3-Pyridin-3-yl-N-[5-(2,3,4-trimethoxy-benzyl)-thiazol-2-yl]-propionamide;
3-(4-Fluoro-phenyl)-N-[5-(2,3,4-trimethoxy-benzyl)-thiazol-2-yl]-propionamide;
3-Biphenyl-4-yl-N-[5-(2,3,4-trimethoxy-benzyl)-thiazol-2-yl]propionamide;
3-(4-Fluoro-phenyl)-N-[5-(4-methoxy-benzyl)-thiazol-2-yl]-2-methyl-propionamide;
N-[5-(4-Fluoro-phenyl)-thiazol-2-yl]-3-phenyl-propionamide;
3-(4-Fluoro-phenyl)-N-(5-phenylsulfanyl-thiazol-2-yl)-propionamide;
N-(5-Phenylsulfanyl-thiazol-2-yl)-3-pyridin-3-yl-propionamide;
3-Phenyl-N-(5-phenylsulfanyl-thiazol-2-yl)-propionamide;
3-(3-Methoxy-phenyl)-N-(5-phenylsulfanyl-thiazol-2-yl)-propionamide;
N-[5-(4-Methoxy-phenylsulfanyl)-thiazol-2-yl]-3-phenyl-propionamide;
N-[5-(4-Methoxy-phenylsulfanyl)-thiazol-2-yl]-3-pyridin-3-yl-propionamide;
3-Biphenyl-4-yl-N-(5-phenylsulfanyl-thiazol-2-yl)-propionamide;
N-{5-[4-(3-Methoxy-phenyl)-piperazin-1-yl]-thiazol-2-yl}-3-phenyl-propionamide.

7. A pharmaceutical composition comprising an inert carrier and an effective amount of the compound according to claim 1.

8. A method for treating cancer wherein the cancer is selected from the group consisting of melanoma, breast cancer, cervical cancer, lung cancer, and colon cancer, comprising administering to a subject in need thereof a composition comprising an effective amount of the compound according to claim 1.

9. A method for inhibiting vascular capillary formation, comprising administering to a subject in need thereof a composition comprising an effective amount of the compound according to claim 1.

10. A method for vascular disrupting, comprising administering to a subject in need thereof a composition comprising an effective amount of the compound according to claim 1.

* * * * *